(12) United States Patent
Folan

(10) Patent No.: US 9,555,116 B2
(45) Date of Patent: Jan. 31, 2017

(54) ANTIMICROBIAL COMPOSITIONS CONTAINING FREE FATTY ACIDS

(71) Applicant: Michael Anthony Folan, Donegal Town (IE)

(72) Inventor: Michael Anthony Folan, Donegal Town (IE)

( * ) Notice: Subject to any disclaimer, the term of this patent is extended or adjusted under 35 U.S.C. 154(b) by 0 days.

(21) Appl. No.: 14/623,850

(22) Filed: Feb. 17, 2015

(65) Prior Publication Data

US 2015/0157720 A1 Jun. 11, 2015

Related U.S. Application Data

(63) Continuation of application No. 13/510,361, filed as application No. PCT/EP2010/067710 on Nov. 17, 2010, now abandoned.

(30) Foreign Application Priority Data

Nov. 17, 2009 (IE) .................................... 2009/0872

(51) Int. Cl.
| | | |
|---|---|---|
| *A01N 43/08* | (2006.01) | |
| *A61K 31/34* | (2006.01) | |
| *A61K 47/12* | (2006.01) | |
| *A61K 31/20* | (2006.01) | |
| *A61K 31/201* | (2006.01) | |
| *A61K 31/685* | (2006.01) | |

(52) U.S. Cl.
CPC ............... *A61K 47/12* (2013.01); *A61K 31/20* (2013.01); *A61K 31/201* (2013.01); *A61K 31/685* (2013.01)

(58) Field of Classification Search
CPC .. A61K 2300/00; A61K 31/20; A61K 31/685; A61K 31/201; A61K 47/12
See application file for complete search history.

(56) References Cited

U.S. PATENT DOCUMENTS

| | | |
|---|---|---|
| 2,864,707 A | 12/1958 | Toulmin |
| 4,005,043 A | 1/1977 | Fusey |
| 4,164,594 A | 8/1979 | Jackson et al. |
| 5,660,858 A | 8/1997 | Parikh et al. |
| 5,731,278 A | 3/1998 | Nair et al. |
| 2001/0051595 A1 | 12/2001 | Lyons et al. |
| 2003/0021850 A1* | 1/2003 | Xu ..................... A61K 31/20 424/520 |
| 2004/0156887 A1* | 8/2004 | Auriou ................ A61K 31/575 424/450 |
| 2005/0042299 A1* | 2/2005 | Folan ..................... A61K 35/20 424/535 |
| 2012/0289591 A1 | 11/2012 | Folan |

FOREIGN PATENT DOCUMENTS

| | | |
|---|---|---|
| CN | 1578670 A | 2/2005 |
| CN | 101442956 A | 5/2009 |
| WO | 03/018049 | 3/2003 |
| WO | 2005/117600 | 12/2005 |
| WO | 2008/043386 | 4/2008 |
| WO | 2009/072097 | 6/2009 |

OTHER PUBLICATIONS

Sprong, C. et al., "Bactericidal Activities of Milk Lipids", Antimicrobial Agents and Chemotherapy, American Society for Microbiology, 45(4): 1296-1301 (2001).
Bergsson, G. et al., "In Vitro Killing of Candida Albicans by Fatty Acids and Monoglycerides", Antimicrobial Agents and Chemotherapy,. 45(11): 3209-3212 (2001).
Kabara, J. et al., "Fatty Acids and Derivatives as Antimicrobial Agents", Antimicrobial Agents and Chemotherapy, 2(1): 23-28 (2001).
Ramadan, M.F. et al., "Antimocribical and Antiviral Impact of Novel Quercetin-Enriched Lecithin", Journal of Food Biochemistry, 33: 557-571 (2009).
Sun, C. et al., "The antimicrobial properties of milkfat after partial hydrolysis by calf pregastric lipase", Chemico-Biological Interactions, 140: 185-198 (2002).
Thormar, H. et al., "Inactivation of enveloped viruses and killing of cells by fatty acids and monoglycerides", Antimicrobial Agents and Chemotherapy, 31(1): 27-31 (1987).
International Search Report received in corresponding International Application No. PCT/EP2010/067710.
Sivasankar, B., Food Processing and Preservation, 2002 by Prentice-Hall on India Private Limited, New Delhi.

* cited by examiner

*Primary Examiner* — Jean Cornet
(74) *Attorney, Agent, or Firm* — Patrick J. Hagan; Dann, Dorfman, Herrell and Skillman, P.C.

(57) ABSTRACT

The invention concerns antimicrobial compositions comprising free fatty acids emulsified with membrane lipids or hydrolyzed derivatives thereof, and pharmaceutical formulations comprising same. The compositions can be used in the treatment of prophylaxis of microbial infections. They can also regulate the rate of blood clotting rendering them suitable for incorporation in catheter locking solutions and for use in wound care.

12 Claims, 6 Drawing Sheets

ANTIMICROBIAL COMPOSITIONS CONTAINING FREE FATTY ACIDS

CROSS-REFERENCE TO RELATED APPLICATIONS

This application is a continuation of U.S. patent application Ser. No. 13/510,361, filed Jul. 31, 2012, which is a 371 of PCT/EP10/67710, filed Nov. 17, 2010, which claims priority to IE 2009/00872, filed Nov. 17, 2009, the entirety of which are incorporated by reference herein.

BACKGROUND OF THE INVENTION

This invention relates to antimicrobial compositions containing free fatty acids and to pharmaceutical formulations containing same.

Free fatty acids are essentially insoluble in water. Their insolubility and the fact that they are incompatible with many conventional excipients have seriously restricted their medicinal use to date. While salts of free fatty acids are soluble in water, they are known to have greatly reduced antimicrobial effect. Several methods have been used to "solubilise" free fatty acids, including the use of alcohols and surfactants and derivitisation by re-esterification to form mono-glycerides and/or ethoxylation and propoxylation procedures.

The antimicrobial properties of free fatty acids have been known for many years (Kabara J. et al. Antimicrobial Agents and Chemotherapy, July 1972; 2(1): pp 23-28).

Bergson et al. (Antimicrobial Agents and Chemotherapy, November 2001, pp 3209-3212), reported that both capric and lauric acid were effective in killing the yeast *Candida albicans*.

Sun et al. (Chemico-Biological Interactions 140 (2002), pp 185-198), identified the superior microbicidal properties of caprylic, capric and lauric acid, concluding that lauric was most potent against gram positive bacteria while caprylic was optimal against gram negative organisms.

The anti-viral properties of free fatty acids were reported by Halldor et al. (Antimicrobial Agents and Chemotherapy; January 1987, pp 27-31).

WO 03/018049 discloses the antimicrobial activity of milk serum apo-proteins in combination with free fatty acids from milk fat. It is illustrated that the adhesion inhibitory properties of milk extracts are exclusively attributable to the water soluble protein fraction, and that the lipid component makes no contribution to this effect.

WO 2009/072097 discloses properties of compositions of free fatty acids such as melting point depression and sequestration which affect antimicrobial potency. Also disclosed are emulsification methods used to incorporate blends of free fatty acids in a milk whey protein isolate.

Sprong et al. (Antimicrobial Agents and Chemotherapy, Vol 45, No 4, 2001, pp 1298-1301), report microbicidal effects for sphingosine and sphingomyelin and some slight effect from lyso-phosphatidyl ethanolamine and lyso-phosphatidyl choline, but no effect was observed from any of the unmodified phopsholipids. It is notable that these results are reported for exposure times in excess of 2 hours at 37° C., in contrast to the present invention where microbicidal effects are shown for combinations of membrane lipids and free fatty acids, for exposure times of less than 5 minutes.

Jones et al: Journal of Pharmacy and Pharmacology, 2003, Vol 55, No 1. pp 43-52 discloses the use of lecithin in combination with cholesterol as a surface coating to inhibit bio-film formation on medical devices.

It is an object of the invention to provide improved antimicrobial compositions containing free fatty acids.

SUMMARY OF THE INVENTION

The invention provides an antimicrobial composition comprising:
(a) one or more saturated or unsaturated free fatty acids having from 4 to 22, preferably 6 to 18 or 6 to 12, carbon atoms or a pharmaceutically acceptable salt or ester thereof; and
(b) one or more membrane lipids or a hydrolysed derivative thereof, as emulsifying agent for the free fatty acid(s) or the salt or ester thereof.

The free fatty acid may be selected from: butyric (C4:0), valeric (C5:0), caproic (C6:0), heptanoic (C7:0), caprylic (C8:0), pelargonic (C9:0), capric (C10:0), undecanoic (C11:0), undecylenic (C11:0), lauric (C12:0), myristic (C14:0), palmitic (C16:0), palmitoleic (C16:1), margaric (C17:0), stearic (C18:0), oleic (C18:1), linoleic (C18:2), linolenic (C18:3), arachidonic (C20:4) and euricic (C22:1).

The free fatty acid is preferably selected from: valeric, caproic, caprylic, pelargonic, capric, undecanoic, undecylenic, lauric, myristic, palmitic, stearic, oleic, linoleic and linolenic acids and mixtures thereof, and pharmaceutically acceptable salts and esters thereof. Particularly preferred are caproic, caprylic, pelargonic, capric, undecylenic and lauric acids, especially caprylic acid.

Where combinations of fatty acids are used including higher melting point entities such as lauric acid, lower melting point entities such as caprylic or oleic are preferably included to depress the melting point of the combination to less than normal physiological temperatures.

DETAILED DESCRIPTION OF THE INVENTION

Membrane lipids are ubiquitous components of all cell membranes in the plant and animal kingdoms. They are characteristically made up of one or in most cases two long chain hydrocarbon molecules attached to a highly polar head group, which is a derivative of either, glycerol-3-phosphate, a long chain amino alcohol (sphingosine), a sugar, or a derivative of a steroid (cholesterol). The properties of each membrane lipid are mainly dictated by the variation in the polar head group. Nearly all are amphoteric in so far as they behave as both acid and base and more importantly all are amphipathic, having a water soluble, hydrophilic end at the polar head group and a fat soluble lipophylic end at the hydrocarbon tail.

The physico-chemical properties of membrane lipids are well known and a suitable review of their occurrence and biological properties may be found in Biochemistry, $3^{rd}$ edition: Mathews, Van Holde & Ahern: ISBN 0-8053-3066-6, from which Table 1 has been collated.

TABLE 1

Major classes of membrane lipids.

| Class of Membrane Lipids | Polar Head group | Membrane Lipids |
|---|---|---|
| Lecithin/Phospholipids/ Glycerophospholipids | Glycerol | Phosphatidic acid<br>Phosphatidylcholine<br>Phosphatidylethanolamine<br>Phosphatidylglycerol<br>phosphatidylinositol<br>Phosphatidylserine |

TABLE 1-continued

Major classes of membrane lipids.

| Class of Membrane Lipids | Polar Head group | Membrane Lipids |
|---|---|---|
| Sphingolipids & glycosphingolipids | Sphingosine | Ceramide<br>Sphingomyelin |
| Glycoglycerolipids | Saccharide | Glycolipids<br>Glycosphingolipids<br>Cerebrosides<br>Gangliosides<br>Glycoglycerolipids<br>Mono-galactosyl diglyceride |
| Cholesterol | Steroids | Lanosterol |

Of the four major classes of membrane lipids those containing phosphate in the polar head group are the most common. Described as glycerophospholipids, phosphoglycerides or more frequently as phospholipids this group makes up the major portion of all membrane lipids in the bacteria, plant and animal kingdoms. All phospholipids are based on a glycerol backbone with two hydrophobic acyl side chains on carbons at sn1 and sn2 and a phosphate moiety at sn3. Variations in the phosphate head differentiate six separate types of commonly occurring phospholipids, the simplest being phosphatidic acid and progressing with increasing complexity through phosphatidylcholine, phosphatidylethanolamine, phosphatidylglycerol, phosphatidylserine, and phosphatidyl inositol, phosphatidylcholine being the most prevalent in animals and bacteria.

All six of the above mentioned phospholipids are found in lecithin, a membrane lipid of commerce which is extracted on industrial scale from a variety of sources including but not limited to soya bean, sunflower, canola, palm oil, egg yolk and butterfat. The term 'lecithin' is frequently used synonymously with the major phospholipid component phosphatidylcholine, which may be purified from crude lecithin, as is usual when rigorous control of quality is required in pharmaceutical applications. It is also possible to enzymatically modify lecithin or any of its component phospholipids by, for example, removing one of the hydrocarbon side chains to form lyso-phospholipids' all of which are equally suitable for use in this invention.

Hydrolysed derivatives of membrane lipids include lyso-phospholipids and lyso-sphingolipids which may be produced enzymatically using pancreatic phospholipases available from Novozyme, Denmark. The process involves preparation of an aqueous dispersion of phospholipids or sphingolipid, addition of phopsholipase enzyme at 2% W/V and incubation at an elevated temperature of from about 50° C. to about 60° C. for about 2 hours. Yield of hydrolysed membrane lipid may be up to 70%, and the product may be separated from the mixture by water partition based on increased hydrophilicity of the lyso derivative.

The membrane lipids used herein may be extracted from plant or animal sources including oil bearing seeds, animal fat, wool, milk and eggs.

The membrane lipids and derivatives thereof used in the present invention are preferably delipidised. As used herein, the term "delipidised" is intended to mean that substantially all of the conjugated extraneous lipid material, such as oil, fat or triglyceride material, with which membrane lipids are normally associated in nature, is removed. "Substantially all" in this context is intended to mean that the delipidised membrane lipid contains less than 10%, preferably less than 5%, more preferably less than 3%, of conjugated extraneous lipid material.

The membrane lipid is preferably selected from one or more of phospholipids, lecithin, glycerophospholipids, sphingolipids, glycosphingolipids, glycoglycerolipids and cholesterols. Suitable membrane lipids include lecithin, phosphatidic acid, phosphatidylcholine, phosphatidylethanolamine, phosphatidylglycerol, phosphatidylinositol, phosphatidylserine, ceramide, sphingomyelin, glycolipids, glycosphingolipids, cerebrosides, gangliosides, glycoglycerolipids, mono-galactosyl diglyceride, lanosterol or cholesterol or any combination thereof. Preferred are lecithin and other phospholipids selected from phosphatidic acid, phosphatidylcholine, phosphatidylethanolamine, phosphatidylglycerol, phosphatidylinositol and phosphatidylserine and mixtures thereof. Lecithin is particularly preferred.

In the antimicrobial composition of the invention, a combination of one or more of caproic, caprylic, pelargonic, capric, undecylenic and lauric acids with one or more phospholipids is particularly preferred, especially caprylic acid with lecithin that is preferably delipidised.

The ratio of free fatty acid or pharmaceutically acceptable salt or ester thereof to membrane lipid may be from about 0.25:1 to about 10:1; or from about 0.5:1 to about 10:1, or from about 0.5:1 to about 5.0:1, or from about 1.0:1 to about 2.5:1, or from about 1.25:1 to about 2.5:1, on a weight for weight basis.

Free fatty acids are negatively affected when in contact with bodily fluids, such as blood, serum or mucus. However, it was unexpectedly found that this effect could be ameliorated in the presence of an organic acid or salt or ester thereof and/or an inorganic acid salt. Thus, the antimicrobial composition of the invention may also comprise one or more pharmaceutically acceptable organic acids or a pharmaceutically acceptable salt or ester thereof; and/or one or more pharmaceutically acceptable inorganic acid salts.

The organic acid is preferably selected from acetic, pyruvic, propionic, glycolic, oxalic, lactic, glyceric, tartronic, malic, maleic, ascorbic, fumaric, tartaric, malonic, glutaric, propenoic, cis or trans butenoic and citric acids and mixtures thereof, and pharmaceutically acceptable salts and esters thereof. The inorganic acid salt is preferably selected from chloride, sulphate and nitrate.

Particularly preferred organic acids are citric and lactic acids and the sodium and potassium salts thereof, especially sodium citrate.

The molar concentration of the organic acid is preferably from about 25 mM to about 500 mM, more preferably from about 50 mM to 250 mM, and more preferably from about 50 mM to 150 mM. The pH of the organic acid salt is preferably between 4.0 and 6.5, preferably between 4.0 and 5.5 or between 4.0 and 5.0.

In the antimicrobial composition of the invention, the membrane lipid emulsifies the fatty acid, rendering it water-dispersible. Thus, the membrane lipid-fatty acid combination is an emulsion, preferably an oil-in-water emulsion, although a water-in-oil emulsion is also possible.

In a particularly preferred embodiment, the composition of the invention comprises an emulsion of 0.5% caprylic acid in 0.4% de-lipidised lecithin, which is then diluted to 50% of its concentration using 200 mM sodium citrate buffer at pH 4.5, the final concentration being 0.25% caprylic acid emulsified in 0.2% de-lipidised lecithin and dispersed in 100 mM sodium citrate at pH 4.5. This composition is referred to hereinafter as the "standard formulation" and may conveniently be used to demonstrate the antimicrobial effects of the inventive compositions.

The antimicrobial compositions of the invention exhibit a dual antimicrobial effect, in that they exhibit inhibition of microbial adhesion to host cell surfaces and achieve a microbicidal effect through dissolution of microbial cell membranes.

It has unexpectedly been found that when membrane lipids are separated from conjugated lipid moieties, different membrane lipids exhibit strikingly different adhesion inhibitory properties on microbial cells in planktonic culture. While not wishing to be bound by theory, it is suggested that these differences arise from variable hydrophobic/hydrophilic characteristics. Furthermore it has been discovered that the same amphipathic variability affects the tenacity of emulsions formed with individual membrane lipids and that these differences can be exploited to manipulate the rate of release of emulsified microbicidal free fatty acids, thereby greatly facilitating the design of fast or slow acting microbicidal formulations with superior utility in medical applications.

As described herein, superior and adjustable adhesion inhibitory properties may be obtained using membrane lipids, particularly phospholipids, collectively described as lecithins, after they have been extracted and freed of conjugated lipid with which they are normally associated in their natural environment. Inhibition of microbial adhesion requires that the lipophylic end of the membrane lipid is free to orientate with and conjugate to lipid moieties on the microbial cell surface. This process is impeded if the lipophylic sites are occupied by non-membrane lipids (triglycerides for example).

A particular utility afforded by the inventive compositions is the discovery that the different classes and different members of each class of membrane lipids have different release characteristics. The same dose of the same fatty acid in the same amount of different membrane lipid will deliver the same microbicidal effect over a faster or slower period depending on the individual membrane lipid. This peculiar characteristic facilitates the use of combinations of different membrane lipid emulsions of the same fatty acid to achieve a sustained release effect over relatively useful periods.

A feature of free fatty acids and particularly the short to medium chain saturated fatty acid, such as caprylic acid, is that they are rapidly absorbed through skin and mucosal membranes. Rapid absorption depletes the dose at the epithelial surface and consequently impairs the microbicidal effect at that surface. For this reason, membrane lipids delivering the most immediate microbicidal effect are not necessarily the most effective in therapeutic applications. As demonstrated hereinafter in Example 9, certain individual membrane lipids are more tenacious than others, which restricts the availability of their emulsified free fatty acid, and consequently restricts the rate of its microbicidal effect, which equally restricts its absorption at the epithelial surface. It should be noted, however, that the overall microbicidal effect (log numbers of microorganisms killed) is not affected.

It has also unexpectedly been found that the antimicrobial compositions of the invention can be used to regulate the rate of blood clotting. By varying the ratio of free fatty acid to membrane lipid and/or by incorporation of pharmaceutically acceptable salts of organic or inorganic acids, or oligosaccharides or other polymers, the formulations will either catalyse the rate of blood clotting or suppress it altogether. This property gives great advantage in use as a blood contact antimicrobial agent.

As disclosed herein, an aqueous dispersion of de-lipidised membrane lipid added to fresh sheep blood at a volume of 20% will accelerate the normal rate of blood clotting, reducing the time to clot from 6 minutes to less than one minute. Addition of a fatty acid, such as caprylic acid, by emulsification up to a ratio of about 1.0-1.3 times the weight of de-lipidised membrane lipid, such as lecithin, will further reduce the time to clot formation, but thereafter as the ratio of fatty acid increases, the time to clot formation is increased and an anti-coagulation effect is observed when the weight of emulsified fatty acid exceeds about 1.0-1.3 times the weight of de-lipidised membrane lipid. A skilled person will appreciate that the blood regulatory effect will depend not only on the ratio of free fatty acid to de-lipidised membrane lipid, but also on the nature of the membrane lipid and free fatty acid used.

The presence of an organic salt in the inventive composition, as might be required for amplification of microbicidal effect, will also destroy the pro-coagulation effect, and as illustrated herein the use of a viscosity-enhancing agent, such as dextran, will extend the anti-coagulation effects to the point where they are comparable with a solution of heparin.

In a further embodiment, an emulsion of free fatty acid not exceeding about 1.0-1.3 times the weight of de-lipidised membrane lipid may be used to enhance the rate of blood clotting and exert an antimicrobial effect at the site of bleeding, while an emulsion of free fatty acid exceeding about 1.0-1.3 times the weight of de-lipidised membrane lipid with or without added salts of organic acids may be used to inhibit blood clot formation and exert a microbicidal effect at the site of bleeding.

The compositions of the invention containing membrane lipid emulsified free fatty acids exert vastly superior dual antimicrobial effects: both inhibition of adhesion and microbicidal effect. One of the significant advantages provided by dual antimicrobial effect is that the adhesion inhibitory properties prevail long after the microbicidal pay-load has been exhausted. Most microbicides are chemically reactive with the target organism and most microbicidal reactions are irreversible under physiological conditions; a fixed dose of a microbicide therefore has a limited reactive capability. In combination with an adhesion inhibitory substance however, the adhesion inhibitory properties persist after the microbicide has been depleted and additional protection is afforded against any residual viable pathogens.

In addition to superior and adjustable inhibition of adhesion combined with superior microbicidal effect and intrinsic blood-clotting regulatory effects, the compositions of the invention are compatible with systemic administration (blood contact), in contrast to milk protein compositions disclosed in WO 03/018049, and WO 2009/072097. Membrane lipids and free fatty acids are natural metabolites in the human and animal body, their antimicrobial effects are concentration dependent and when they enter the systemic circulation they are rapidly diluted, metabolized and excreted as natural metabolites.

The use of membrane lipids in combination with an antimicrobial agent is counter-intuitive, as most conventional antimicrobial agents are inactivated by lecithin and related membrane lipids; lecithin is listed as an approved antiseptic neutralizing agent for use in European Standard EN 1499 and 1500 testing for evaluating the microbicidal effect of hand soaps and gels.

The compositions of the invention may be used in the treatment or prophylaxis of microbial infections in humans or animals. Due to the regulatory effect on blood-clotting, the compositions may be used in, for example, catheter locking solutions and in wound care.

The invention also provides a pharmaceutical formulation comprising a composition according to the invention and a pharmaceutically acceptable carrier, diluent or excipient therefor. The composition may be present in the pharmaceutical formulation in an amount of from about 0.1% to about 25% (w/v); or from about 0.1% to about 10% (w/v); or from about 0.1% to about 1.0% (w/v).

The pharmaceutical formulation may be in any form suitable for administration to a human or animal, including for example, forms suitable for oral, topical, enteral, parenteral or mucosal administration.

The formulation of the invention can be used as a topical antimicrobial agent for prevention and treatment of infections of the skin, hair, nails and external membranes of the body orifices.

The inventive composition or formulation may be used in the construction of a liquid soap or hand gel for elimination of asymptomatic carriage of potentially pathogenic bacteria such as methicilin resistant *Staphylococcus aureus* and other species commonly associated with nosocomial or hospital acquired infections. It may be used as a gel for treatment of acne. It may be used in the form of an ointment for treatment of dermatophytic fungal infections of the hair follicles including that caused by Trychophyton species commonly known as ringworm. It may be constructed in the form of a spray for delivery to the skin as a treatment for infections caused by the enveloped viruses including Herpes varieties causing cold sores and shingles. It may be prepared in the form of liquid drops for treatment of infections of the eye and ear. It may be prepared in a variety of pharmaceutically acceptable delivery systems for treatment of infections of the mucosa including the mucosal surfaces of the nose, mouth, throat, bronchiole and lungs and the gastro-intestinal tract and genitalia. It may for example be prepared in the form of a toothpaste and mouthwash to facilitate improved dental hygiene and eliminate the burden of organisms causing dental caries, gum disease, aphthous ulcer and halitosis. It may be prepared in a form suitable as a saliva supplement for alleviation of the symptoms of xerostomia. It may be prepared as a spray for de-colonisation of the mouth, throat and nasal membranes, particularly for eradication of asymptomatic carriage of antibiotic resistant species. It may be prepared in the form of a gel for the prevention and treatment of microbial infections of the genitalia caused by a variety of bacteria, yeast and viruses including those known to be the causative agents of Candidiasis, non-specific bacterial vaginosis, the herpes virus and HIV. It may be prepared in the form of an enema for prevention and treatment of infections of the bowel and lower intestinal tract including those caused by anaerobic *Clostridium* species and Desulfovibrio medically known as pseudomembraneous colitis and pouchitis.

Membrane lipid emulsified free fatty acids may be used to prepare foods that exert an antimicrobial effect in the gastro-intestinal tract, serving to protect against enteric pathogens such as *Helicobacter, E. coli, Salmonella, Campylobacter, Clostridium* species, Protozoa and enveloped viruses.

A suitable food carrier for membrane lipid emulsified free fatty acids is dairy milk, preferably fat free dairy milk and more preferably skim milk powder such as Marvel, available commercially from Premier International Foods (UK) Ltd, Spalding, Lincolnshire, England.

Separate emulsions of, for example, caprylic, capric and lauric acids may be prepared as 5.0% W/V emulsions in 4.0% W/V de-lipidised lecithin as described in the methods. The individual emulsions may be combined in a ratio of 1:1:1 or any other suitable ratio such as 1:2:3. Membrane lipid emulsions of other fatty acids such as butyric and or emulsions of essential oils such as peppermint or vanilla may be added to impart flavour and improve taste.

Marvel skim milk powder may be re-constituted by adding the specified amount to potable water (4 heaped teaspoons to one pint). To this an amount from about 1% W/V to 15% W/V of a selected ratio of membrane lipid emulsified free fatty acids may be added and mixed by stirring. Preferably the amount of emulsified fatty acid will be from about 1% W/V to 10% W/V and more preferably about 5% W/V. It will be clear to a skilled person that skim milk powder may be re-constituted in less than the optimal volume of water for use as milk, in which case a concentrated dairy cream is formed to which amounts of emulsified fatty acids may be added.

Alternatively, a dairy whey protein isolate may be used as a suitable food carrier: Provon 190 from Glanbia PLC is a suitable whey protein isolate. The whey protein isolate may be re-hydrated in potable water in an amount of from about 10% W/V to 20% W/V, preferably about 15% W/V. Once fully hydrated, an amount of membrane lipid emulsified free fatty acid or blend thereof may be added and mixed by stirring. When whey protein isolate is used as a carrier, the amount of added membrane lipid emulsified free fatty acid may be from about 1% W/V to 20% W/V, preferably from about 5% W/V to 15% W/V and more preferably about 10% W/V.

The products of the invention have utility as blood contact antimicrobial agents where their combined blood clotting or anti-clotting capability is combined with their antimicrobial effects. Such uses include surgical irrigation, wound care, catheter locking solutions, the coating of catheters and other tubular surgical devices for insertion into a bodily orifice or cavity, and in food safety.

A significant advantage of the products of the invention is that very short exposure times are required to achieve an antimicrobial effect, generally less than 1 hour or less than 30 minutes or less than 10 minutes.

As used herein and in conventional use, the term 'antimicrobial' refers to any substance, component or composition of components which exhibit an antagonistic effect towards protozoa, gram positive and negative bacteria (both aerobes and anaerobes), yeast, fungi, mycoplasma and/or viruses and in particular those microbial species that are capable of causing disease in humans and animals.

Infectious disease arises either from ingress of pathogenic microbial species (microorganisms) from the external environment or as a result of aberrant growth of microorganisms that are normally present in the natural micro-flora of the skin, hair, and mucosal membranes of the eye, nose, mouth, gastro-intestinal tract and the genitalia.

Whether exogenous or endogenous it is widely understood among healthcare professionals that the first stage of microbial pathogenesis involves adhesion of the microorganism to the surface of human or animal tissue. Once adhered, colonization takes place by way of proliferation and further adherence after which toxin production inflammation and destruction of host tissue give rise to the classical symptoms of infectious disease. It is also widely accepted that if adhesion can be prevented, initiation of the pathogenic process can be inhibited and many infectious diseases could be prevented or at least limited in the scope of their proliferation.

The novel properties of membrane lipid emulsified free fatty acids present wide ranging utility in human and animal healthcare. In blood contact applications these include surgical irrigation fluids, haemostatic antimicrobials in wound care, catheter coatings and catheter locking solutions for prevention of catheter related bacteraemia; in mucosal healthcare they can be used to replicate the natural antimicrobial mechanism of healthy mucus; in topical skin care they can be used to amplify the natural antimicrobial defenses of the skin; in food safety because they are natural metabolites they can be applied directly to a food surface to eradicate food borne pathogens; and as medical foods they can be used to supplement a normal diet to prevent or treat infections of the gastro-intestinal tract.

Surgical Irrigation and Wound Care

During surgical intervention it is common practice to employ a variety of techniques to minimize the ingress of potentially pathogenic bacteria, yeasts, moulds and viruses. A common and growing problem is the potential infection of an open wound by antibiotic resistant bacteria such as Methicillin Resistant *Staphylococcus Aureus* (MRSA), and many others including but not limited to *Enterococcus* species, *Pseudomonas*, and the yeast *Candia albicans*. In many cases open wounds are irrigated to clear them of loose tissue, blood and other body fluids and in many cases a solution of sterile saline is currently in use, although this offers no antimicrobial effect. The use of surgical irrigating fluids containing antibiotics is not recommended simply because these have the potential to generate further antibiotic resistant species. Equally, many conventional antiseptic agents are unsuitable and potentially toxic in direct systemic contact with an open wound. There is therefore a great need for a safe and effective antimicrobial irrigating fluid, preferably one which has the additional optional properties of inhibiting blood clotting during microsurgery and/or a companion product which can promote blood clotting and healing after surgery. Compositions based on optionally de-lipidised membrane lipids combined with free fatty acids and/or derivatives thereof as described herein provide such utility. Also in trauma care after accidental injury or during military operations, wounds are frequently jagged, dirty and possibly hemorrhaging profusely. There is a great need for emergency intervention with antimicrobial products that promote blood clotting and which can be applied safely to an open wound.

Prevention of Catheter Related Infection

In simplistic terms a catheter is a tube inserted through the skin, into an artery or vein or through a natural orifice for the purpose of draining body fluids, or for administration of drugs or for the purpose of monitoring disease or manipulation of surgical instruments. Some catheters remain in place for relatively long periods of time, and in many cases these are susceptible to microbial contamination causing bio-film on the inside and outside surfaces and potentially leading to disseminated infection of the patient.

The most common catheter is a urinary tract tube with a collecting vessel to drain urine from the bladder; these are recognized as being significant sources of hospital acquired infection. A more elaborate and complicated system is a central venous catheter (CVC) inserted either through the jugular vein in the neck and threaded through to the superior vena cava at the heart or inserted through a peripheral vein and threaded through to the same vein draining into the heart. CVCs are designed to be left in place for extended periods of up to 90 days or more and are intended for long term repetitive infusion of drugs and/or nutritional formulations; in such applications they are routinely opened for administration and closed again for intermittent periods during which fluid in the lumen of the catheter is static and susceptible to microbial growth if contaminated. Accidental contamination of CVCs is relatively common and frequently gives rise to catheter related blood stream infections which are potentially fatal.

Blood enters the lumen of a CVC during routine medical procedures, where it clings to the inside and may clot blocking the lumen. A blocked CVC lumen necessitates catheter replacement under surgery which adds greatly to time, cost and patient mortality.

A catheter locking solution (CLS) is a volume of fluid sufficient to fill the lumen of the catheter between medical procedures. An optimal CLS will exert an antimicrobial and anti-coagulation effect. Currently there are a number of proprietary CLS formulations on the market that are designed to achieve both prevention of blood clotting and an antimicrobicidal effect. The selection of active ingredients to construct these CLS formulations is constrained by the risk of accidental intra-venous infusion. The void volume of a CVC may be as much as 3.0 ml or more. In the event that a medical administrator forgot that a locking solution had been inserted and accidentally added a second dose, the first void volume would be infused directly into the blood stream where it could have serious toxicological implications for the patient.

The formulations herein may be in the form of catheter locking solutions, which can achieve optimal microbicidal effect in less than 1 hour and have anti-clotting properties similar to heparin without the use of that material in the formulation. The catheter locking solutions preferably have a viscosity approximating to that of whole blood to minimize the potential for dilution and mixing at the catheter tip. The desired viscosity can be achieved using viscosity-enhancing agents.

Viscosity-enhancing agents routinely used in pharmaceutical preparations include a wide range of hydrogels of natural or synthetic origin. Included among these are derivatives of cellulose such as carboxymethyl cellulose and hydroxyethyl cellulose. Other natural polymers of plant origin include dextran, alginate, pectin, guar gum and acacia gum; synthetic polymers include a range of carbomers (acrylates/C10-30 alkyl acrylate cross polymers) and Poloxamers (triblock copolymers of polyoxyethylene and polyoxypropylene). For reasons of residual toxicity and metabolic clearance, few of these are approved for routine systemic use in human medicine. The Poloxamer, Pluronic F68 has been used in parenteral nutrition formulations, but the naturally occurring dextran has achieved more extensive use in surgery.

In the formulations of the invention, dextran is the preferred viscosity-enhancing agent. Dextran is a naturally occurring polysaccharide. A complex branched glucan of glucose monomers, it is produced by many bacteria including Leuconstoc species, and it has been used as an irrigant and anti-clotting agent in micro-surgery. Dextran is available commercially in a range of molecular weights ranging from 10 Kilo daltons (Kd) to 150 Kd. In the invention, 20 Kd to 60 Kd dextran is preferred. More preferably, 40 Kd dextran is used to adjust the viscosity of a membrane lipid/free fatty acid-based catheter locking solution to approximate to that of whole blood: 3.6-6.5 cP.

When 40 Kd dextran is used as viscosity-enhancing agent, its concentration in formulations should preferably be from about 5% to 50% on a weight by volume basis, more preferably from about 10% to 40%, and more preferably still from about 15% to 30% weight by volume based on the entire formulation.

Table 2 below provides a summary of the more common proprietary CLS formulations currently in use:

TABLE 2

Proprietary CLS Formulations currently in use or under development

| Proprietary Brand | Known Active Ingredients | Reported Efficacy |
|---|---|---|
| Duralock MedComp, Philadelphia USA | 47.6% Tri-sodium citrate | Anti-coagulant, microbistatic not microbicidal |
| Zuragen Ash Access Technologies Lafayette, Indiana, USA | 7% sodium citrate 0.05% Methylene Blue 0.15% Methyl Parabens 0.015% Propyl Parabens | Anti-coagulant Microbicidal over 12 hours |
| Taurolock Tauropharm AG, Waldebuttelbrunn Germany | 1.35% Taurolidine 4% sodium citrate | Anti-coagulant Microbicidal over 12 hours |
| Canusal Wockhardt UK LTD Wrexham Wales | 0.9% saline 200 I.U. heparin/ml | Anti-coagulant Not microbicidal |

Most of the lock solutions in use currently have relatively low microbicidal effect: reduction in microbial viability of 3-4 logs in more than one hour exposure. As disclosed herein, a CLS based on membrane lipid emulsified free fatty acids exhibits superior antimicrobial effect eradicating greater than 6 logs in less than 6 minutes. Optimal anticoagulation effects are achieved by modifying the ratio of membrane lipid and free fatty acid and the optional use of a viscosity-enhancing agent eliminates migration of blood into the catheter tip. Greater safety in the event of accidental double locking is assured by the fact that the components used in this invention are natural metabolites.

Antimicrobial Surface Coating

The compositions of this invention can be used to create dual action anti-adhesion and antimicrobial surface coatings by trapping a film of free fatty acid, on any animate or inanimate surface, including but not limited to skin, plastic, rubber, metal or glass, wherein they exert a microbicidal effect at the surface in addition to repelling adhesion of microbial species.

Active antimicrobial surface coatings have particular application in healthcare, for prevention of bio-film formation on medical instruments and on catheter surfaces, and also as a surface coating for work stations, procedural trays and all patient contact surfaces, including the hands of healthcare workers. Similarly, active antimicrobial surface coatings have extensive application in the food industry where they can be applied to food preparation and packaging surfaces to minimize carriage of food borne pathogens such as *Salmonella, Campylobacter, Listeria* and *E. coli* and as demonstrated herein, they can also be applied to the surface of food products, particularly post-slaughter meat, to eradicate these pathogens at source.

Conventional surface antisepsis is achieved using an antiseptic wipe which may contain triclosan, chlorhexidine, quaternary ammonium compounds or a concentrated solution of alcohol. However, the residual toxicity of many conventional antiseptics limits their use on food and animate surfaces.

When used in surface coating applications, the composition of the invention may be applied in a suitable pharmaceutically acceptable delivery system, with or without other excipients. Pharmaceutically acceptable delivery systems include, but are not limited to, organic solvents designed to evaporate on application leaving a dry residue, liquids, creams, gels, pastes, ointments, powders or sprays and include combinations of these with insoluble materials such as fibrous wipes.

Mucosal Fortification:

The mucus membranes of humans and animals are characteristically moist surfaces at the interface of natural body orifices, and the lining of the gastro-intestinal tract and the genitalia, they include the eye, nose, inner ear, mouth, naso-pharyngeal surfaces, trachea, bronchioli, esophagus, stomach, large and small intestines, rectum, vagina and external labia, the glans and the lining of the urinary tract. In addition to these anatomically related surfaces that are common to humans and animals, there are mucosal structures that are unique to particular species such as the guttural pouch in equids.

Mucus membranes are covered by a layer of mucus, a viscous hydrocolloid comprised mainly of mucins, a group of heavily glycosylated high molecular weight proteins which act as a matrix within which many other biologically active materials are dispersed including secretory antibodies and components of the innate immune system such as histatins and statherins in saliva. In addition to hydration and lubrication, mucus is essential for prevention of ingress of potential microbial pathogens and for prevention of adhesion and colonization of the mucus membranes themselves.

Impairment of mucosal secretions and debilitation of the integrity of the mucus itself may arise as a consequence of disease, or as a side effect of medical and/or pharmaceutical intervention or as a consequence of life-style. Where this happens, those afflicted suffer from recurring mucosal infection including but not limited to dental caries, gum-disease, oral thrush, yeast vaginitis, bacterial vaginosis, enteritis and infectious colitis. The complexity of mucus has defied all attempts to construct exact replicas which may be used in replacement therapy. There are a number of commercial substitutes, which are designed to relieve the pre-dominant physical symptoms of oral dryness. Most of these are based on hydro-gels such as carboxymethyl cellulose and a composition of salts to affect buffering and re-mineralisation. One is based on pig-gut mucin (Saliva Orthana, AS Pharma, Eastbourne, UK), but none approximate to the natural adhesion inhibitory aspects of saliva and mucus in general. The combined adhesion inhibitory and microbicidal properties of the inventive formulations, particularly tailored release formulations as disclosed herein, offer superior mimicry of the antimicrobial properties of natural mucus.

Topical Disinfection and Skin Care

The skin, hair and nails of mammals, being the external body surfaces are subject to constant environmental contamination. Healthy mammalian skin has intrinsic antimicobial properties based on naturally occurring free fatty acids in the skin, and these may be advantageously fortified by topical application of delipidised membrane lipid-emulsified free fatty acids as disclosed herein.

Bacteria causing skin infection include, but are not limited to, *Staphylococcus aureus, Streptococus pyogenes* and *Pseudomonas areruginosa*, causing Impetigo, Folliculitis, Erysipilis, Cellulitis and Necrotising Fasciitis. Propionibacteriium acne is the causative agent of juvenile acne. Fungal skin infections are caused mainly by *Trichophyton, Microsporum* and *Epidermophyton* species and the diseases are known collectively as Tinnea (pedis, cruris, capitis, corporis and unguinium) which include ringworm and nail infections. Yeast including *Candida albicans* cause Intertrigo and Paronychia; *Malassezia furfur* causes Tinnea versicolor (seborrheic dermatitis and infectious dandruff) and it is also a common ailment in dogs' ears. Enveloped viral infections include Herpes Simplex Type 1 affecting orofacial regions and type 2 affecting the genital regions. Herpes zoster causes shingles and the poxvirus causes Molluscum contagiosum. Superficial asymptomatic carriage of HIV, SARS, Hepatitis, Swine flu', bird flu' and many other zoonotic viral infections may also be eliminated using the compositions herein.

There is significant public concern about the increasing incidence of hospital acquired infection (HAI). HAI include infections caused by antibiotic resistant bacteria such as Methicilin Resistant *Staphylococcus aureus* (MRSA), and Vancomycin Resistant Enterococci (VRE) and other multi-drug resistant species such as *Clostridium difficile* and other less well known opportunistic pathogens including *Pseudomonas* and *Candida.*

It is well known that hand antisepsis is critical in preventing cross-contamination between patients and patient care staff. Most patient care establishments routinely use an alcohol gel for hand antisepsis. Alcohol is an immediate and potent microbicidal agent. It evaporates within seconds however, leaving no persistent effect to protect against accidental contamination that might happen immediately after evaporation. Membrane lipid emulsions of free fatty acids may be tailored in a manner that provides a sustained release of microbicidal effect and when formulated with alcohol, the effect is both immediate and persistent.

Food Safety

It is well known that many food animals harbour food borne pathogens, primarily in their gut, but also on their skin from contamination with faeces. Conventional antiseptics and antibiotics are not suitable for liberal topical or systemic application to animals before slaughter, or to their meat after slaughter. The individual components that make up the products of this invention, however, have the advantage of being used routinely in parenteral nutrition; in separate constructs therefore they have been deemed to be non-toxic, and their suitability for use topically on fresh meat is disclosed herein.

Food borne pathogens include *Salmonella, Escherichia, Campylobacter* and *Clostridium* species. The efficacy of the products of this invention in vitro is demonstrated in the Examples. Methods of eradication of food borne pathogens at primary processing of meat include the proposed use of carcass washing with a suitable antimicrobial agent. Other methods of application that are relevant to food safety include the use of membrane lipid-emulsified free fatty acids as surface coatings for food packaging using procedures similar to those described for application of antimicrobial surface coatings to medical devices.

Methods and Materials:

Emulsification Procedures

Free fatty acids greater than C6 are insoluble in aqueous media. Membrane lipids are equally insoluble in water but may be dispersed therein, and under appropriate conditions combinations of free fatty acids and membrane lipid may be induced to form emulsions in water. These are either oil-in-water or water-in-oil emulsions, the latter having the higher relative concentration of fatty acid by weight.

A water-in-oil (free fatty acid) emulsion may be prepared by dissolving e.g. about 1 gram of membrane lipid, such as optionally delipidised lecithin, in about 2 grams of free fatty acid. Stir for about 10 minutes and then add about 2 grams of sterile distilled water, agitate vigorously by shaking for 30 seconds and allow to hydrate for 30 minutes. When fully hydrated the emulsion has a thick creamy consistency which may be further diluted with up to 20 ml of water, added in 5 ml aliquots with intermediate agitation by shaking. An excess of water added to this emulsion will cause it to break and invert in part or in whole and become unsuitable for further processing.

Oil-in-water emulsions are better suited to high water content applications such as wound dressings, catheter locking solutions and surface disinfection, as described hereinafter. Methods of preparing oil-in-water emulsions are well known to those skilled in the art and are disclosed in, for example, WO2009/072097.

A suitable example of an oil-in-water emulsion of free fatty acid in membrane lipid may be prepared by suspending a suitable quantity of membrane lipid, such as optionally delipidised lecithin, in sterile distilled water, and stirring this at room temperature for about 30 minutes with a magnetic stirrer to ensure even dispersion. Using a suitable dispersing device, the desire amount of free fatty acid, such as caproic, or caprylic, or pelargonic acid, is slowly added while vigorously agitating the volume of dispersed membrane lipid. The amount of membrane lipid (e.g. lecithin) is conveniently 0.4 g in 100 ml water, to which 0.5 g of free fatty acid can be added using e.g. a 5-ml syringe or pipette. A laboratory homogenizer such as an Ultra-Turax Model T18 (IKA Works, Wilmington, N.C. 28405, USA) fitted with an S18N-19G dispersing tool, operating at 6,000 to 8,000 RPM, is a preferred method of agitation. The resulting emulsion is a thin white liquid suspension of free fatty acid, which is stable and can be diluted many-fold without de-stabilising the emulsion.

A similar procedure may be used to prepare an oil-in-water emulsion of, for example, capric acid or undecylenic acid, provided the constituents are first equilibrated at 37° C., or above their melting point. Once emulsified, the emulsion remains stable on cooling below the melting point of the incorporated free fatty acid and may be diluted further for use in formulation.

A membrane lipid emulsion of lauric acid may be prepared in a similar manner provided all constituents are first equilibrated at 50° C. or above the melting point of lauric acid, and again this emulsion will remain stable on cooling and in further dilution for use in formulation.

Free fatty acids have limited microbicidal effect at temperatures below their individual melting point. This fact has little significance for those acids with melting points below normal physiological temperatures (37° C.), except in situations where such emulsions may be required to exhibit an effect in hypothermic conditions.

Blends of high and low melting point free fatty acids have depressed melting points due to the solvent effect of the lower melting point constituent. A combination of lauric acid with a melting point of 44° C. and caproic acid with a melting point of −3.4° C. in a 50:50 ratio, will exhibit a combined melting point of 26° C., and the blend may be emulsified as described above at temperatures above 26° C.

Higher melting point free fatty acids may also be dissolved in low melting point blends of essential oils or other neutral oils to achieve a depression of melting point suitable for antimicrobial use under physiological conditions. Essential oils are hydrophobic constituents extracted from many different plants by distillation or solvent extraction. They are widely used commercially as perfumes and in fringe medical practice such as aromatherapy. Most notable examples include oil of clove, orange, lemon, lavender, juniper, and rose. Many of these are known to exhibit microbicidal effect in their own right; oil of lemon balm for example is recognized as being an effective viricidal agent and when used as a solvent for higher melting point fatty acids such as lauric acid, the combined microbicidal and viricidal properties provide expanded utility in medical applications.

Oil of lemon balm will dissolve up to 40% by weight of lauric acid at 20° C. and the blend may be emulsified in membrane lipid such as lecithin, as described above.

Oil-in-water emulsions of free fatty acids or blends thereof may be prepared in concentrations of optionally de-lipidised membrane lipid ranging from about 0.1% to 10% and emulsified free fatty acid loadings of from 0.1 to 10%. The loading may conveniently be 4% membrane lipid such as lecithin, and 5% free fatty acid or blend thereof. More preferably still a loading of 0.4% optionally de-lipidised lecithin and 0.5% free fatty acid or blend thereof is used, which may be diluted further for use in formulation.

The microbicidal efficacy of any membrane lipid emulsion of free fatty acid according to the invention is amplified by increasing surface area of the emulsified droplet; relative surface area is increased by decreasing the droplet size. Droplet size is a function of the amount of energy imparted by the dispersing tool during the emulsification procedure. Generally, finer droplets may be produced using higher homogenization speeds and the use of an ultrasonic probe adjacent to the emulsification head will also facilitate smaller droplets and increased surface area.

De-Lipidisation of Membrane Lipids

De-lipidisation can be achieved by suspending the membrane lipid or hydrolysed derivative thereof in a polar solvent, such as an alcohol or ketone, at a concentration of about 10% w/v and stirring for about 30 minutes during which time extraneous lipid is dissolved. Membrane lipids are insoluble in polar solvents and will readily settle out after stirring allowing the polar solvent with its dissolved lipid to be decanted. Residual solvent is allowed to evaporate in e.g. a fume hood. Suitable solvents include acetone and ethanol.

Adhesion Assay:

A suitable model of microbial adhesion and inhibition of adhesion is provided by the interaction between the yeast *Candida albicans* and human Buccal Epithelial Cells freshly harvested from the inside the cheek.

In the assay procedure, a standardized population of fresh late log-phase *Candida* are exposed to a variable concentration of test substance for 10 minutes, then combined with a fixed ratio of buccal epithelial cells (BECs) for 60 minutes, during which time yeast will adhere to the BECs to a greater or lesser degree depending on the potency of the inhibitory substance used in pre-treatment. After the adhesion period, the combined yeast and BECs are diluted by a factor of 2× in sterile buffer and agitated briefly (5 seconds) on a laboratory vortex. Wet mount samples of the mix were examined under a microscope using 400× magnification. Yeast cells adhering to BECs are clearly visible and enumeration of these is facilitated using dark field conditions; the use of a Neubauer hemocytometer slide facilitates counting. In total 100 BECs are evaluated and the total number of yeast adhering to these is used as the sample count. The control is equivalent to 100% adhesion and reduction in this number in response to test item or protein blank is reported as percent inhibition of adhesion.

Buccal epithelial cells are harvested from the inner cheek mucosa of volunteers by rubbing a sterile tongue depressor in a circular fashion and rinsing the collected cells into 5 ml of sterile phosphate buffered saline (PBS). BECs should preferably be collected in the morning before eating or brushing teeth. Donations from 4-5 volunteers are needed to achieve five assay points.

BECs are pooled and counted using direct microscopic count with a hemocytometer slide; a count of 500/ml (for example) may be achieved. The pooled sample is centrifuged at 1,500 RPM for 3 minutes, and re-suspended in a volume of sterile PBS, calculated to achieve a concentration of 500 BECs per ml. This concentrate was divided into 2.5 ml aliquots in 10 ml centrifuge tubes and centrifuged again at 1,500 RPM for 3 minutes. The supernatant is discarded and the cell pellets held on ice pending their use in the rest of the assay.

The yeast used in these assays is a fresh clinical isolate of *Candida albicans*; ATCC 10231 may be used as an alternative, but all culture collection 'Type' strains have lost some virulence and do not adhere as well as fresh isolates.

Yeast cells are maintained on yeast extract peptone dextrose (YEPD) agar, and a loop-full of a pure culture is used to inoculate a 250 ml Erlenmeyer flask containing 100 ml of sterile YEPD broth. The inoculated flasks are incubated overnight (10-14 hours) at 37° C. in an orbital incubator at 100 RPM. YEPD is: 2% W/V glucose, 1% W/V Yeast Extract, 1% W/V bacteriological peptone, Agar where required at 1-2% W/V, all from Oxoid, UK.

The late log-phase cells are counted with a hemocytometer slide and the concentration adjusted to 100× the test concentration of BECs (40,000/ml in these examples), using 50 mM sodium lactate buffer pH 4.5. 2.5 ml aliquots of the standardized suspension of yeast are washed once by centrifugation with sodium lactate buffer at 4,000 RPM and held as a pellet pending the assay procedure as described below. A solution of test substance and protein blank at the required concentration is prepared in 50/100 mM sodium lactate buffer pH 4.5 or sodium citrate buffer pH 4.5; unless otherwise stated, citrate or lactate buffers on their own were used as controls to determine full adhesion. Bovine serum albumin (BSA) is used as a protein 'blank', Sigma-Aldrich A-7030; St Louis Mo., USA. The material is crude, "initial fractionation by heat-shock" as non-heat shocked fractions may contain active serum immunoglobulin which may contribute to the inhibition of adhesion.

Washed yeast pellets from above are re-suspended in 2.5 ml volumes of test, blank or control solutions and held at 37° C. for 10 minutes pre-treatment. Each 2.5 ml volume of test, blank or control (with yeast in suspension) is then used to re-suspend a pellet of washed BECs from above. The combined suspensions are then incubated with gentle agitation at 37° C. for 60 minutes. The use of an orbital incubator at 50 RPM provides a suitable environment.

After incubation, 2.5 ml of 50 mM sodium lactate buffer at pH 4.5 is added to each of the test solutions mixed and subjected to a 5 second pulse on a laboratory vortex. The purpose of the final dilution and vortexing is to separate loosely adhering yeast and yeast cells that are lying adjacent to, but not attached to, BECs. Further dilution may be necessary to facilitate counting of adherent yeast.

The assay may be performed as a pre-treatment of BECs by reversing the order of re-suspension described above. BECs are first re-suspended in 2.5 ml volumes of control buffer, test or protein blank, held at 37° C. for 10 minutes and then used to re-suspend a pellet of washed yeast and the procedure completed as described above.

Assay of Microbicidal/Microbistatic Effect:

The assay is a standard microbiological suspension test wherein known concentrations of late log phase bacteria, yeast or fungi are inoculated into a fixed volume or weight of a test substance, blank or control. After a set period of time a neutralizing solution is added to stop the antimicrobial effect and the residual population of viable microorganisms is enumerated by serial dilution and plate counting. The counting procedure is a standard and basic microbiological procedure for enumerating viable microorganisms and will be well known to those skilled in the art.

In its generic form the method requires inoculation of 1 gram or 1 ml of test sample with 0.1 ml of 18 hour (late log phase) followed by vigorous agitation to mix. After the predetermined exposure time has elapsed, 9.0 ml of neutralizing buffer is added and mixed. This has the effect of stopping the microbicidal effect which allows reliable estimates to be made of the percentage kill achieved by a particular test sample in the period between inoculation and neutralization. Typically exposure periods will range from 30 seconds up to 30 minutes and may progress to several hours where that time period is required to measure the effect. In order to enumerate residual viable cells and from that to compute percentage kill, serial dilutions and plate counts are carried out on the 10 ml sample plus neutralizing buffer.

In the assays herein, stocks of bacteria, yeast and fungi are routinely stored on beads in 50% glycerol at −80° C. When required for viability/microbicidal assay, small aliquots from these stocks are spread on an appropriate nutrient agar, grown and sub-cultured to ensure purity. Where broth cultures are required, 250 ml Erlenmeyer flasks containing 100 ml of broth are inoculated with a transfer loop from pure agar cultures and incubated under constant agitation in a rotary incubator at 37° C.

Bacteria are routinely cultured using brain heart infusion (BHI) broth and agar or tryptone soya agar or broth (TSB), both of which may be acquired commercially from Oxoid, UK. TSB has the following constituents: 1.5% W/W tryptone (pancreatic digest of casein), 0.5% W/W peptone (papaic digest of soybean meal), 0.5% W/W sodium chloride, and agar at 1.5% WAN when required as a solid medium. Yeast are grown on YEPD agar or broth (see adhesion assay method hereinabove).

The diluting and neutralizing buffers used in the present method are phosphate buffered saline (PBS), containing 137 mM sodium chloride, 2.7 mM potassium chloride and 10 mM phosphate, to which is added 3% polysorbate Tween 80 (anionic surfactant), 0.3% lecithin, and 0.5% histidine as neutralising agents. These 'neutralising' agents are those prescribed under EU Guidelines for ISO certification of microbicidal efficacy and were validated as suitable for neutralizing free fatty acids and chorhexidine at the concentrations used herein.

Some microbial species are extremely difficult to culture, requiring specialized media and/or anaerobic conditions which are not easily achieved in liquid culture. *Clostridium difficile* for example is an anaerobe and also aero-intolerant dying off quickly in the presence of oxygen. Fungal pathogens such as the Trychophyton species grow in hyphal mode and cannot be enumerated using the standard serial dilution procedure. In order to evaluate the microbicidal effect of the inventive product against these species, agar dilution techniques were used and plate culture evaluated to find the minimum inhibitory concentration, i.e. that concentration of product above which no growth was observed.

The technique requires preparation of 10× concentrations of the test formulation for dilution in 9 volumes of agar. A 4 ml aliquot of this 10× concentrate was added to 16 ml of cooled sterile agar and dispensed to a Petri dish—this represented the full strength (100%) formulation in the agar medium, which may then be expressed as the percentage concentration of microbicidal fatty acid in agar. Further dilutions of the 10× concentrate with sterile distilled water and the use of 4 ml aliquots of these dilutions in 16 ml of cooled agar allowed the preparation of a series of decreasing concentrations of the product in agar. The test organisms were inoculated onto these agars with a sterile loop and the minimum inhibitory concentration was determined as the lowest dilution of test item at which no growth was detectable.

Inhibition of Biofilm Formation:

Bio-film is an attachment and accretion of planktonic bacteria, yeast and/or fungi to solid surfaces. The attachment is usually facilitated through exo-polysaccharides secreted by the microorganisms and studies suggest that it happens more easily on hydrophobic surfaces, such as plastic, and less easily on hydrophilic surfaces such as steel. The formation of bio-film is highly significant in medical science, particularly its formation on the surface of indwelling catheters, where it can be the source of catheter-related blood stream infections. Many different microbial species are capable of forming bio-film, in medicine. However, those of greatest significance are *Staphylococcus aureus, Staphylococcus epidermidis, Enterococcus faecalis, Escherichia coli, Klebsiella pneumoniae, Pseudominas aeruginosa* and the yeast, *Candida albicans*.

The model of biofilm formation used herein is based on the method of Christensen et al. J. Clin. Microbiol. 22: 996-1006, where growth of a selected organism and its biofilm formation in microtitre plate wells is measured by staining with crystal violet and measuring the intensity (Optical Density) of the stained biofilm in a microtitre plate reader at 570 nm wavelength. The intensity of the stain is a measure of the extent of biofilm formation and its reduction in the presence of inhibitory substances is evaluated on the basis of reduction of the stain intensity.

The organism used in this assay is *Staphylococcus aureus* RN4220, a restriction deficient variant derived originally from NCTC 8325 known for its avidity in biofilm formation, particularly in the presence of excess levels of sodium chloride which is added to the culture media to promote that feature, culture media is 3.7% BHI from Oxoid UK to which 4% W/V NaCl is added.

Nunc microtitre plate wells (Nunc International, Rosskilde, Denmark) are coated with the test sample and 1:100 dilutions of late log phase bacteria in fresh saline supplemented BHI are dispensed to each test well, and incubated for 24 hours to facilitate biofilm formation.

On completion of the incubation period, the wells are rinsed three times with sterile distilled water, and dried for one hour at 60° C. to fix the adhering biofilm. Staining is achieved using a 0.4% solution of crystal violet which is added to each well and agitated there by rocking the plate for 4 minutes. Excess dye is removed and the plates are rinsed three times with sterile distilled water and dried. When dry, the intensity of the stain in each well is measured using a ASYS Hitech UVM-340 plate reader at 570 nm (ASYS, Eugendorf, Germany).

Manipulation of Hemostasis: Clotting/Anti-Coagulation of Blood

Hemostasis is the inherent ability of the blood to react to traumatic damage by forming a clot to plug the wound and so prevent excessive loss of blood and facilitate tissue repair and healing of the wound. Hemostasis also refers to the inherent ability of the blood to remain liquid in undamaged blood vessels and so fulfill its primary physiological transport functions. Both of these hemostatic aspects can become defective in disease and both can be overwhelmed by traumatic damage, either accidentally or by default during surgical intervention.

The ability to manipulate the hemostatic mechanism by either amplifying the rate of clotting to prevent blood loss after accidental trauma or to prevent clotting during surgical repair and/or to prevent clot formation on, or in, surgically inserted medical instruments including catheters, is of great importance in medicine. To measure the rate of blood clotting herein, use is made of a whole blood clotting meter, the Hemochron Signature 11, manufactured by ITC, International Technidyne Corporation, Edison, N.J., USA. The meter uses customized cuvettes into which one drop of fresh blood may be added and the time taken for clot formation is measured optically and reported electronically by the device.

In the assay herein, fresh sheep blood was used, which was drawn from a jugular vein using an 18 gauge needle and suitable volume syringe. Fresh blood samples are immediately mixed with a volume of test material at varying concentrations and one drop inserted in the cuvette. Sterile phosphate buffered saline is used as a blank to obviate the effects of dilution and heparin is used as a control anticoagulant. Measurement of the anti-clotting effects of the products of the invention are evident in seconds compared to untreated whole blood, and compared to the anti-clotting effect of heparin and other proprietary anti-clotting (anti-coagulation) products. In optimal configuration the products of the invention achieve an anti-coagulation effect lasting in excess of 1,000 seconds, which is comparable to 5,000 I.U of heparin under similar test conditions.

Measurement of accelerated clotting time (amplified clotting) is not possible using the Hemochron device, as in most cases the products of the invention achieve clotting in under 60 seconds, which is 'off scale' for the meter.

Comparative measurement of accelerated clotting times is achieved using appropriate volumes of fresh blood mixed with a volume of test material, where the combined volumes totalled 5 ml in each case in a 15 ml graduated Greiner centrifuge tube (Greiner Bio-one, North Carolina, USA). Immediately after addition of fresh blood, the tubes are inverted twice to mix and allowed to stand without further agitation. Clot formation is visibly apparent when the tubes are tilted slightly, and once a clot formed its integrity was such that it would remain suspended when the tubes were inverted. In each test a 5 ml sample of fresh whole blood (undiluted) is used as a control.

Analysis of Membrane Lipid and Free Fatty Acid

Routine analytical High Performance Liquid Chromatography is a suitable method of analyzing the individual membrane lipid components in a composition such as lecithin. The procedure is well known to those skilled in the art of analytical chromatography. A Waters 2420 ELSD HPLC system from Waters Corporation, Milford, Mass., USA is used herein. A Symmetry C8 column (3.0×150 mm, 5 micron column is suitable with a non-linear gradient of 82% methanol in water containing 0.1% tri-fluoroacetic acid and gives adequate separation of membrane lipid components.

Mammalian Cell Viability.

The reduction in viability of mammalian cells in the presence of membrane lipid emulsified free fatty acids was evaluated using Raji B lymphocytes grown in RPMI 1640 media containing 10% fetal calf serum and Gibco Penstrep 15140 antibiotic supplement. Mature cells are harvested by centrifugation at 1,000 RPM for 3 minutes and re-suspended in RPMI 1640 without supplements for test purposes. Toxicity is assessed by evaluating uptake of trypan blue dye by dead cells using an Invitrogen Countess Automated Cell Counter (Invitrogen Inc, Carlsbad, Calif., USA). The procedure involves exposing a population of Raji B cells to the test solution by mixing 100 µl of test and cell suspension in a microtitre plate well. After a pre-determined period of exposure, 10 µl of cell and test mix are combined with 10 µl of 0.4% trypan blue and 10 µl of this added to the chamber of a cell cytometer cuvette and evaluated in the cell counter described above. Results are provided as a total cell count and numbers of these that are alive or dead are based on uptake or exclusion of the dye; a percentage viability is computed automatically.

Figure 1:
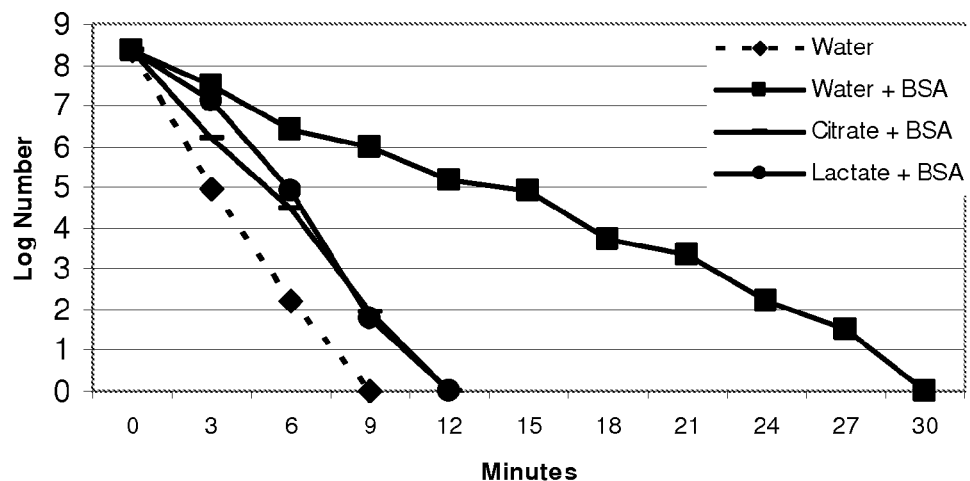
FIG. 1 illustrates the antimicrobial inhibitory effect of blood serum and the counteraction of this effect in combination with salts of organic acids, as described in Example 3.

The practical applications and benefits of this invention are illustrated further in the following Examples. Unless otherwise stated, the membrane lipids used in the Examples are delipidised and contain less than 3% conjugated extraneous lipid material as shown by HPLC analysis as described in the Methods.

Example 1

Preparation of Adhesion Inhibitory Compositions of Membrane Lipids

The following membrane lipids were purchased from Sigma Aldrich, Poole, Dorset, UK.

TABLE 3

Membrane lipids

| Membrane lipid | Compound/Component | Original source | Code |
|---|---|---|---|
| Phospholipid | Crude Lecithin | Soya Bean | LC |
| Phospholipid | Phosphatidylcholine | Soya Bean | PTC |
| Phospholipid | Phosphatidylethanolamine | Soya Bean | PTE |
| Phospholipid | Phosphatidylglycerol | Soya Bean | PTG |
| Phospholipid | phosphatidylinositol | Soya Bean | PTI |
| Phospholipid | Phosphatidylserine | Soya Bean | PTS |
| Sphingolipid | Ceramide | Bovine Brain | C |
| Sphingolipid | Sphingomyelin | Bovine Brain | SGM |
| Glycoglycerolipid | Mono-galactosyl diglyceride | Wheat flour | MGDG |
| Cholesterol | Lanosterol | Sheep wool | L |

Crude lecithin was purchased from GR Lane Ltd, Gloucester, UK.

Aqueous dispersions of each of the above membrane lipids were prepared by suspending 1.0 grams in 100 ml of sterile distilled water (10 mg/ml) and agitating therein for 60 minutes with the aid of a magnetic stirrer. Dispersion of ceramide, sphingomyelin and lanosterol was achieved with the aid of sonication and stirring, while dispersion of all other membrane lipids was relatively easily achieved with stirring alone. Phospholipid and glycoglycerolipid dispersions were relatively stable, but others had a tendency to separate on standing and so all dispersions were subjected to 30 seconds homogenization using a laboratory homogenizer immediately prior to use in the adhesion inhibitory assay. A suitable homogeniser is an Ultra-Turax Model T18 (IKA Works, Wilmington, N.C. 28405, USA) fitted with an S18N-19G dispersing tool, operating at 6,000 to 8,000 RPM.

The adhesion inhibitory properties of each phospholipid were tested as described in the methods at concentrations of 10, 5, and 2.5 mg/ml; the lower dilutions were achieved by diluting the original dispersion with sterile distilled water. Due to logistical limitations of collecting sufficient buccal epithelial cells at any one time, the assays were conducted in blocks of five individual membrane lipids on separate days, and the results shown in Table 4 are a composite of these; the Control is zero concentration of test item and Bovine Serum Albumin (BSA) is used as a protein blank.

TABLE 4

*Candida albicans* per 100 Buccal Epithelial Cell

| Item Code | 0 mg/ml | 2.5 mg/ml | 5.0. mg/ml | 10 mg/ml | % inhibition at 2.5 mg/ml |
|---|---|---|---|---|---|
| LC | 540 | 387 | 291 | 92 | 28 |
| PTC | 540 | 127 | 59 | 0 | 76 |
| PTE | 496 | 167 | 74 | 0 | 66 |
| PTG | 496 | 114 | 62 | 0 | 77 |
| PTI | 519 | 201 | 87 | 0 | 61 |
| PTS | 519 | 233 | 102 | 39 | 55 |
| C | 484 | 363 | 282 | 109 | 25 |
| SGM | 484 | 379 | 277 | 126 | 21 |
| MGDG | 540 | 261 | 128 | 66 | 51 |
| L | 519 | 306 | 236 | 133 | 41 |
| BSA | 496 | 400 | 379 | 303 | 19 |

In preliminary evaluation of crude lecithin from various sources (egg yolk, soya and sunflower), it was noted that the adhesion inhibitory properties varied considerably, despite the reported purity being approximately the same. It was reasoned that the purchased material might contain extraneous fat or tri-glyceride and to remove this, the original material was suspended in acetone at 10% W/V and stirred for 30 minutes after which the insoluble membrane lipid was allowed to settle and the acetone decanted. The 'de-lipidised' lecithin (DLL) was dried in a fume hood, and its adhesion inhibitory properties evaluated as previously described. The remaining membrane lipids listed in Table 4 were delipidised in the same manner. The delipidised membrane lipids were analysed by HPLC as described in the Methods, and all were shown to contain less than 3% conjugated extraneous lipid material. The results are shown in Table 5 below, including the incremental increase in adhesion inhibitory effect achieved by de-lipidisation of individual membrane lipids.

TABLE 5

*Candida albicans* per 100 Buccal Epithelial Cell

| Item Code | 0 mg/ml | 2.5 mg/ml | 5.0 mg/ml | 10 mg/ml | % inhibition at 2.5 mg/ml |
|---|---|---|---|---|---|
| LC | 540 | 387 | 291 | 92 | 28 |
| DLL | 489 | 138 | 48 | 0 | 71 (+43) |
| DL PTC | 508 | 132 | 0 | 0 | 84 (+8) |
| DL PTE | 515 | 139 | 0 | 0 | 73 (+7) |
| DL PTG | 474 | 57 | 0 | 0 | 88 (+11) |
| DL PTI | 519 | 68 | 0 | 0 | 77 (+16) |
| DL PTS | 519 | 145 | 62 | 0 | 72 (17) |
| DL C | 493 | 305 | 118 | 41 | 38 (+13) |
| DL SGM | 511 | 301 | 133 | 44 | 41 (+20) |
| DL MGDG | 516 | 206 | 116 | 0 | 60 (+9) |
| DL L | 536 | 247 | 91 | 49 | 54 (+13) |
| DL BSA | 513 | 431 | 393 | 329 | 16 (−3) |

Solvent de-lipidisation increases the adhesion inhibitory properties of membrane lipids, especially lecithin by a factor of 2.5, bringing it in line with that of its individual components: PTC, PTE, PTG, PTI and PTS. Further de-lipidisation of the individual components of lecithin achieves further improvement in the adhesion inhibitory properties of these, although less dramatic compared to the effect achieved in de-lipidising crude lecithin. It is assumed here that the commercial process of isolation used to extract individual components of lecithin results in almost complete de-lipidisation, hence the optimal inhibitory effect of these relative to the 'crude' lecithin and the smaller incremental effect achieved by additional de-lipidisation.

In many of the applications for the product of this invention the adhesion inhibitory substance will be in contact with blood serum, mucus and other body fluids. It has been discovered that de-lipidised lecithin and most of its constituents lose their adhesion inhibitory properties in the presence of Bovine Serum Albumin (BSA). It has also been discovered however, that adding an organic acid counteracts this negative effect and restores most of the adhesion inhibitory properties to the combined membrane lipid and BSA.

In this example, 100 mM solutions of sodium lactate and sodium citrate were used. The salts were prepared first as 200 mM solutions and the pH adjusted to 4.5, and aliquots of both were used to prepare 1% solutions of bovine serum albumin (i.e. 1% BSA in 200 mM sodium salt of citrate or lactate at pH 4.5). The salt solutions were used to dilute a 1% suspension of de-lipidised lecithin (DLL) and a 1% suspension of phosphatidyl choline (PTC), to achieve preparations of 0.5% DLL and 0.5% PTC in 100 mM sodium lactate/sodium citrate at pH 4.5 with 5% BSA in each. A further dilution of the membrane lipid suspension to 0.5% with water and the use of this in halving dilutions of salt solution containing 0.5% BSA gave a composition of 0.25% membrane lipid in 100 mM salt with 0.25% BSA. Similar procedures were used to prepare 0.25% and 0.5% solutions of BSA in water and in 100 mM organic salt solution: the results are presented in Table 6.

TABLE 6

Candida albicans per 100 Buccal Epithelial Cell

| Item Code | 0 mg/ml | 2.5 mg/ml | 5.0 mg/ml | 10 mg/ml | % inhibition at 5 mg/ml |
|---|---|---|---|---|---|
| LC: water | 540 | 387 | 291 | 92 | 46 |
| DLL: water | 489 | 138 | 48 | 0 | 90 |
| DLL + BSA water | 396 | 320 | 280 | ND | 30 |
| DLL + BSA Sod' Citrate | 396 | 290 | 144 | ND | 63 |
| DLL + BSA Sod' Lactate | 396 | 340 | 164 | ND | 58 |
| PTC: water | 540 | 127 | 59 | 0 | 90 |
| PTC + BSA water | 474 | 392 | 344 | ND | 28 |
| PTC + BSA Sod' citrate | 474 | 273 | 162 | ND | 66 |
| PTC + BSA Sod' Lactate | 474 | 291 | 138 | ND | 70 |
| BSA Sod' citrate | 474 | 393 | 369 | ND | 22 |

TABLE 6-continued

Candida albicans per 100 Buccal Epithelial Cell

| Item Code | 0 mg/ml | 2.5 mg/ml | 5.0 mg/ml | 10 mg/ml | % inhibition at 5 mg/ml |
|---|---|---|---|---|---|
| BSA Sod' Lactate | 474 | 408 | 372 | ND | 21 |
| BSA: water | 496 | 438 | 400 | 362 | 12 |

In this Example, with the exception of crude lecithin, all of the membrane phospholipids tested were shown to have superior inhibitory properties preventing *Candida albicans* adhesion to Buccal Epithelial Cells. When de-lipidised with acetone, crude lecithin is as inhibitory as its main membrane phospholipid components. In combination with bovine serum albumin, the adhesion inhibitory property is eradicated, but it can be restored in the presence of 100 mM solutions of organic acid salts at acid pH.

Example 2

Preparation and Testing of Microbicidal Combinations of Membrane Lipid and Free Fatty Acid The microbicidal effect of 0.5% caprylic acid in 0.4% de-lipidised lecithin, prepared as described in the Methods, against a range of microbial species may be demonstrated using the microbicidal suspension test described in the Methods. The potency of this material is such that complete eradication of an inoculum in excess of 6 logs may be anticipated in less than 6 minutes. Gram negative species are slightly more resistant than gram positives, particularly those known to be slime producers, such as *Escherichia coli* and *Pseudomonas fluorescens*, where it is thought that the slime layer protects from contact with the fatty acid for some additional minutes.

Table 7 below illustrates the reduction in viability of a range of bacteria and yeast. Because the inoculums vary, the latest time to achieve 50% in viability of the inoculum is provided in the last column (L. T. 50%), as a comparative measure of potency against that particular species.

TABLE 7

Microbicidal Effect: 0.5% Caprylic in 0.4% DLL

| Organism | Gram | Exposure Time | | | | | | | L.T. 50% |
| | | 0 | 60 | 120 | 180 | 240 | 300 | 360 | |
|---|---|---|---|---|---|---|---|---|---|
| Staph aureus RN4220 | +ve | 8.53 | 5.22 | 3.71 | 1.61 | 0 | 0 | 0 | <120 |
| Staph epidermidis NCTC 11047 | +ve | 8.27 | 4.96 | 2.67 | 0 | 0 | 0 | 0 | <120 |
| Strep pyogenes NCTC 8198 | +ve | 7.91 | 5.32 | 3.33 | 1.49 | 0 | 0 | 0 | <120 |
| Strep faecalis NCTC 12697 | +ve | 8.11 | 4.98 | 2.54 | 1.66 | 0 | 0 | 0 | <120 |
| E. coli ATCC 11698 | -ve | 8.43 | 7.17 | 6.2 | 5.28 | 3.64 | 1.79 | 0 | <240 |
| Salmonella typhimurium NCTC 74 | -ve | 7.76 | 5.94 | 3.52 | 2.27 | 0 | 0 | 0 | <120 |
| Klebsiella aerogenes NCTC 9528 | -ve | 6.93 | 5.15 | 3.37 | 1.99 | 0 | 0 | 0 | <120 |
| Proteus mirabilis C.I. | -ve | 7.41 | 6.61 | 5.89 | 3.75 | 1.59 | 0 | 0 | <240 |
| Enterobacter Cloacae C.I. | -ve | 8.62 | 6.54 | 4.94 | 2.32 | 0 | 0 | 0 | <180 |
| Pseudomanas aeruginosa ATCC 27853 | -ve | 8.33 | 7.13 | 5.48 | 4.78 | 2.92 | 1.23 | 0 | <240 |

TABLE 7-continued

Microbicidal Effect: 0.5% Caprylic in 0.4% DLL

| Organism | Gram | Exposure Time | | | | | | | L.T. 50% |
|---|---|---|---|---|---|---|---|---|---|
| | | 0 | 60 | 120 | 180 | 240 | 300 | 360 | |
| *Pseudomanas fluorescens* NCTC 10038 | −ve | 7.29 | 6.42 | 5.13 | 3.63 | 1.29 | 0 | 0 | <240 |
| *Candida albicans* C.I. | Yeast | 6.86 | 4.39 | 2.96 | 0 | 0 | 0 | 0 | <120 |
| *Candida glabrata* NCPF 8750 | Yeast | 6.74 | 4.19 | 2.23 | 0 | 0 | 0 | 0 | <120 |
| *Crypto' neoformans* C.I. | Yeast | 5.97 | 4.11 | 2.96 | 0 | 0 | 0 | | <120 |

Note
C.I = Clinical Isolate
Note:
L.T 50% is Latest Time to achieve 50% reduction in viability in this test The numerical data presented are log numbers where the integer is the log and the decimal the colony count at that log: $6.3 \times 10^5$ for example is presented as 5.63 and this convention will be used throughout this document.

For reasons of difficulty in culturing or because of special growth requirements the potency of the formulation against anaerobes is determined by the Minimum Inhibitory Concentration procedure as described in the Methods, and the results are presented in Table 8.

TABLE 8

Minimum Inhibitory Concentration of 0.5% Caprylic in 0.4% DLL against anaerobes and fungal pathogens using agar dilution technique: MIC value is the % of Caprylic acid in the test plate

| Organism | Notes | MIC |
|---|---|---|
| *Clostridium perfringens* ATCC 43150 | G −ve anaerobe | >0.1 |
| *Clostridium difficile* ATCC 43598 | G −ve anaerobe (aero intolerant) | >0.1 |
| *Bacterioides fragilis* ATCC 43859 | G −ve obligate anaerobe | >0.2 |
| *Fusobacterium nucleatum* NCTC 10652 | G −ve anaerobe: 3 weeks Columbia blood agar | >0.3 |
| *Desulfovibrio desulfuricans* | G −ve anaerobe | >0.1 |
| *Porphyromonas gingivalis* | G −ve obligate anaerobe | >0.1 |
| *Campylobacter jejunii* | G −ve microaerophilic | >0.075 |
| *Actinobacillus actinomycetemcomitans* | G −ve microaerophilic | >0.1 |
| *Corynebacterium diphtheriae* | G +ve facultative anaerobe | >0.1 |
| *Treponema denticola* | Obligate anaerobe | >0.2 |
| *Mycobacterium tuberculosis* | Aerobic acid fast *bacillus* 6 weeks on Lowenstein-jensen medium | >0.2 |

Example 3

Membrane Lipid Antimicrobials in Blood Contact Applications

In common with the negative effect on adhesion inhibitory properties reported in Example 1, the presence of bovine serum albumin also impacts on the microbicidal effect. However as in Example 1, this can be overcome by incorporation of an organic acid salt, at acid pH.

An oil-in-water emulsion of 0.5% caprylic acid in 0.4% de-lipidised lecithin is used in this Example. 200 mM solutions of glycolic, acetic, lactic, and citric acids were adjusted to pH 4.5 using 200 mM sodium hydroxide. 10% W/V solutions of Bovine Serum Albumin were prepared in each of the organic acid salts and in water as a control. 5 ml aliquots of the 0.5% caprylic emulsion were added to 5 ml aliquots of each salt solution with and without BSA, and in water with and without BSA, resulting in dispersions of 0.25% caprylic emulsion in 0.2% de-lipidised lecithin dispersed in 100 mM salt solution at pH 4.5 in each test sample.

*E. coli* was selected for this Example as it has been demonstrated to be one of the most resistant species. The bacterium was cultured in Brain Heart Infusion broth for 18 hours at 37° C. 10 ml fractions of each test sample were inoculated at time zero with 1.1 ml of the overnight culture, and 1.0 ml samples removed from this at 3 minute intervals for residual viability determination using serial dilution and plate counting procedures.

TABLE 9

Antimicrobial effect is impaired by blood components and re-instated by combination with salts of organic acids
0.25% Caprylic in 0.2% De-lipidised Lecithin +/− 5% Bovine Seum Albumin

| | 0 | 3 | 6 | 9 | 12 | 15 | 18 | 21 | 24 | 27 | 30 | kill time |
|---|---|---|---|---|---|---|---|---|---|---|---|---|
| Water | 8.37 | 4.97 | 2.23 | 0 | 0 | 0 | 0 | 0 | 0 | 0 | 0 | 9 |
| Water + BSA | 8.37 | 7.51 | 6.42 | 5.98 | 5.17 | 4.93 | 3.72 | 3.33 | 2.21 | 1.49 | 0 | 30 |
| Glycolate | 8.37 | 5.25 | 2.68 | 0 | 0 | 0 | 0 | 0 | 0 | 0 | 0 | 9 |
| Glycolate + BSA | 8.37 | 6.62 | 5.35 | 3.79 | 2.41 | 1.56 | 0 | 0 | 0 | 0 | 0 | 18 |
| Acetate | 8.37 | 5.94 | 4.21 | 1.28 | 0 | 0 | 0 | 0 | 0 | 0 | 0 | 12 |
| Acetate + BSA | 8.37 | 7.41 | 6.93 | 5.24 | 4.53 | 3.47 | 2.18 | 1.34 | 0 | 0 | 0 | 24 |

TABLE 9-continued

Antimicrobial effect is impaired by blood components and re-
instated by combination with salts of organic acids
0.25% Caprylic in 0.2% De-lipidised Lecithin +/− 5% Bovine Seum Albumin

|  | 0 | 3 | 6 | 9 | 12 | 15 | 18 | 21 | 24 | 27 | 30 | kill time |
|---|---|---|---|---|---|---|---|---|---|---|---|---|
| Citrate | 8.37 | 4.9 | 2.7 | 0 | 0 | 0 | 0 | 0 | 0 | 0 | 0 | 12 |
| Citrate + BSA | 8.37 | 6.2 | 4.5 | 1.93 | 0 | 0 | 0 | 0 | 0 | 0 | 0 | 12 |
| Lactate | 8.37 | 5.29 | 3.19 | 0 | 0 | 0 | 0 | 0 | 0 | 0 | 0 | 9 |
| Lactate + BSA | 8.37 | 7.1 | 4.9 | 1.8 | 0 | 0 | 0 | 0 | 0 | 0 | 0 | 12 |

In a water diluent the effect of 5% W/V BSA is to reduce potency of 0.25% caprylic acid by a factor of 3: Kill Time is extended from 9 minutes to 27. In combination with 100 mM sodium salts of citrate and lactate acids at pH 4.5, the kill time is 12 minutes, glycolate is 18 minutes and acetate is 24. The results of combination with citrate and lactate acid salts with and without BSA are presented in Table 9 above and illustrated in FIG. 1.

Example 4

Use in Food Safety

In this Example 1 cm$^3$ sections of fresh beef were deliberately contaminated with late log phase cultures of *Salmonella enterica* and *Escherichia coli* 0157:H7 at room temperature and allowed to adhere there for 60 minutes. Confirmation of contamination was obtained by mechanically macerating the meat sections in sterile phosphate buffered saline (PBS) and enumeration by serial dilution and plate counting.

A suitable but not optimal carcass wash was prepared using 0.5% caprylic acid in 0.4% de-lipidised lecithin and diluting that ×2 with 200 mM sodium citrate at pH 4.5 as described in Example 3. The wash was sprayed onto contaminated sections of fresh beef, and the antimicrobial effect evaluated by mechanical maceration, serial dilution and plate counting. The results are presented in Table 10 below:

TABLE 10

Reduction in Viability of Pathogens on Fresh Beef

| Time | *Escherichia coli* | | *Salmonella enterica* | |
|---|---|---|---|---|
| minutes | Untreated | Treated | Untreated | Treated |
| 0 | 7.14 | 6.96 | 6.91 | 6.61 |
| 30 | 6.98 | 5.61 | 6.37 | 4.59 |
| 60 | 6.56 | 3.89 | 6.71 | 7.73 |
| 90 | 6.82 | 2.19 | 6.52 | 1.29 |
| 120 | 6.69 | ND | 6.28 | ND |

Note:
ND = Not detected

It should be appreciated that the rate of kill on a porous surface such as meat is extended due to the nature of the surface and the time required to permeate it.

Example 5

Use of Membrane Lipids to Manipulate Blood Clotting Time

As described in this Example the membrane lipid products used may be tailored to affect the rate of blood clotting in addition to contributing a significant antimicrobial effect.

Rate of blood clotting was determined using freshly aspirated sheep blood and apparatus and procedures described in the Methods section. An activated blood clotting meter was used to measure anti-clotting effects and a visual tube comparison to evaluate reduced clotting times.

It was unexpectedly discovered that an aqueous dispersion of de-lipidised lecithin (DLL) will amplify the rate of blood clotting in a concentration dependent manner. Varying concentrations of dispersions of DLL were prepared by suspending the required weight in a volume of water, stirring for 30 minutes to hydrate and homogenizing the suspension with a laboratory homogenizer.

Blood clotting and/or anti-clotting effects were assessed using a 20% ratio of test item to fresh blood: in practice 4.0 ml of fresh sheep blood was added to tubes containing 1.0 ml of test item, inverted twice to mix and then either left standing for visual assessment of reduced clotting time or a single drop was applied to the cuvette of an activated blood clotting apparatus for assessment of anti-clotting effect (extended time to clot formation).

As the concentration of DLL in the test item increases, the observed rate of blood clotting increases, i.e. time to clot formation decreases from 360 seconds for whole blood to approximately 60 seconds or less at DLL concentrations in excess of 1%.

The addition of caprylic acid by emulsification in DLL will also amplify the clotting effect up to a point where the concentration by weight equals or slightly exceeds the concentration of DLL by weight. At 0.5% DLL on its own, the clotting time is approximately 125 seconds. Addition of emulsified caprylic acid up to 0.5% does not significantly affect the clotting time. Between 0.5% and 0.75% caprylic acid there is a further depression of clotting time from 125 seconds to approximately 40 seconds (70% less). Thereafter, however, the anti-clotting effect is reversed and clotting time increases with increasing concentration of caprylic acid.

When the concentration of DLL is reduced to 0.25% with increasing concentration of caprylic acid, there is no significant reduction of clotting over and above that attributable to DLL on its own. In fact, as the concentration of caprylic increases to between 0.75% and 1.0%, the clotting time is restored to normal (360 seconds). Further increasing the relative ratio of caprylic acid in 0.25% DLL, has an anti-clotting effect.

Figure 2:
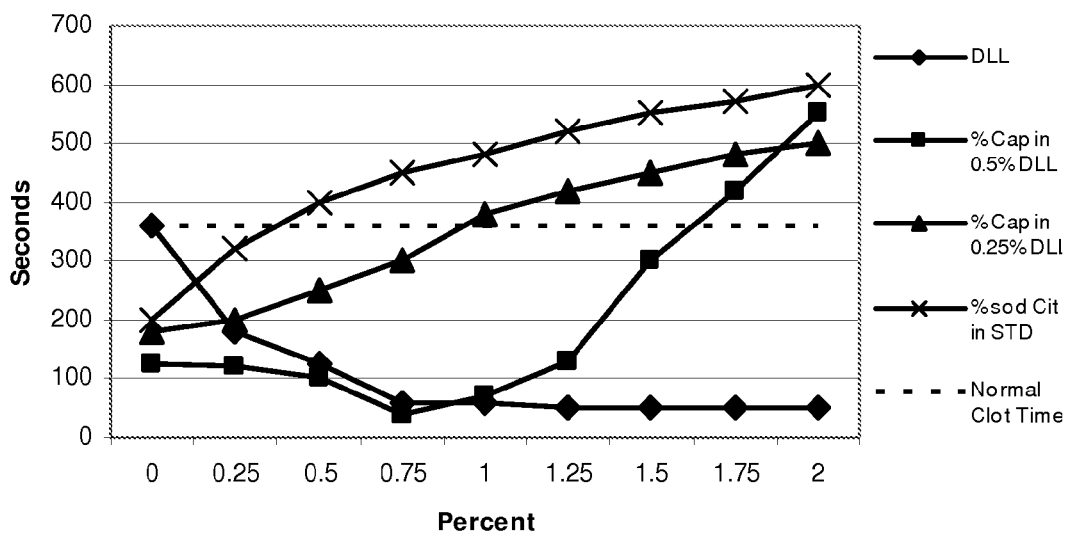
FIG. 2 illustrates blood clotting and anti-clotting properties of varying components of a product according to the invention, as described in Example 5.

Using an emulsion of 0.25% caprylic acid in 0.25% DLL as a standard (STD), it can also be observed that addition of increasing concentrations of sodium citrate salts at pH 4.5 suppresses the anti-clotting effect of DLL in combination with caprylic acid. At 0.5% concentration, the anti-clotting effect of 0.25% caprylic acid in 0.25% DLL has been suppressed completely and clotting time has been restored to above normal (400 seconds). A further increase of sodium citrate in this composition has a progressively increasing anti-clotting effect—up to 600 seconds at 2% sodium citrate in 0.25% caprylic emulsified in 0.25% DLL. The results are illustrated in FIG. 2.

Example 6

Use of Antimicrobial Membrane Lipids in Amplified Clotting for Wound Care

The combined antimicrobial and clot forming capability of the products of the invention are demonstrated in this Example. A suitable, example of an antimicrobial membrane lipid preparation with enhanced clot forming properties may be selected from the combinations prepared in Example 3. A 0.5% dispersion of DLL in sterile distilled water with 1.0% caprylic acid was used here. It will be noted that no organic acid salt is included in this example and further noted that the absence of such reduces the antimicrobial potency but does not limit the clotting effect. The use of a relatively high caprylic acid load compensates for the interference of blood components with the antimicrobial effect.

A bacterial inoculum of E. coli was grown in Brain Heart Infusion broth for 18 hours and a 10 ml volume of this was sedimented by centrifugation at 4,000 RPM for 10 minutes, the pellet was re-suspended in 1.0 ml of the supernatant (concentration×10).

Two 4.0 ml samples of fresh blood were dispensed to two 15 ml Greiner centrifuge tubes and both were inoculated with 0.1 ml of concentrated E. coli suspension: a blank comprising 5.0 ml of 5% Bovine Serum Albumin in sterile distilled water was inoculated at the same time.

A 1.0 ml of volume of 400 I. U. heparin and 500 I. U. streptokinase in water was added to
the first tube, and 1.0 ml of test preparation to the second. Both tubes were mixed by inversion and incubated at 37° C. for 45 minutes. The tube containing the test preparation clotted in approximately 60 seconds; no clot was detectable in the heparin/streptokinase tube after 45 minutes.

At the end of the 45 minute incubation a 1.0 ml of volume of 400 I. U. heparin and 500 I. U. streptokinase in water was added to the clotted tube with test preparation and 1.0 ml of sterile distilled water added to the second. Both samples were homogenized at 1,000 RPM for 2 minutes using an Ultra Turax homogenizer. The clot disruption procedure took approximately 15 minutes (60 minutes exposure in total), after which serial dilution and plate counting procedures were used to enumerate residual bacterial viability in all three tubes.

The BSA blank contained $6.4 \times 10^7$ viable E. coli cells per ml, the control blood (heparin/streptokinase treated) sample contained $8.3 \times 10^5$, and no viable bacteria were recovered from the test sample.

It will be clear to those skilled in the art that preparations such as described in this Example may be applied to wounds in the form of a liquid, spray, gel, powder, or wet-bandage. It will also be clear to those skilled in the art that the preparations described may be added to other pro-coagulants such as chitin, kaolin or alginate to enhance their pro-coagulation effect and add a microbicidal effect.

Example 7

Use of Antimicrobial Membrane Lipids with Anti-Clotting Effect in Surgical Procedures Ingress of potentially infectious agents during surgical procedures is a major cause for concern among healthcare professionals. The use of irrigating fluids with antimicrobial effects facilitates prevention of this. There are also many surgical procedures where the ability to prevent blood clotting is advantageous, micro-surgery procedures for example, where pre-emptive clotting may be exacerbated by the implements used and where the use of an irrigating solution to wash out blood and body fluids to prevent occlusion of the site is desirable. A specialized application is the use of anti-clotting liquids to fill the void volume of indwelling catheters during periods when the catheter is not in use.

In this Example, a dispersion of 0.4% de-lipidised lecithin (DLL) with 0.5% caprylic acid emulsified therein is prepared as described in the Methods. The emulsion is diluted to 50% of its initial concentration with 200 mM sodium citrate at pH 4.5, the result being 0.25% caprylic acid, 0.2% DLL in 100 mM sodium citrate, or approximately 2.5% W/V sodium salt of citric acid at pH 4.5. Sodium citrate is prepared by adjusting the pH of 200 mM citric acid with 200 mM sodium hydroxide to 4.5; this is not the same as 'tri-sodium citrate' which is commonly used as an anti-clotting agent, because not all of the carboxylic acid residues have been salted out.

As described hereinabove, the use of a viscosity-enhancing agent to adjust the viscosity of the formulation to approximate to that of whole blood provides a distinct advantage in preventing dilution of a catheter locking solution at the catheter tip due to blood flow turbulence. Dextran 40 is used here as a viscosity-enhancing agent where it has been found that 20% W/V inclusion provides a viscosity of approximately 4 cP, the viscosity of human blood being between 3.6 and 6 cP.

The emulsified free fatty acid/membrane lipid catheter locking solution used here (ML CLS) has the following constituents: 0.2% W/V de-lipidised lecithin; 0.25% caprylic acid; 20% dextran 40, in 100 mM (2.5% W/V) sodium citrate, pH 4.5. Aliquots of this formulation were dispensed to 15 ml Greiner centrifuge tubes in the following amounts: 0, 0.25, 0.5, 0.75 and 1.0 ml amounts. To each of these 5.0, 4.75, 4.5 and 4.25 ml aliquots of fresh sheep blood were added, respectively. Each tube was evaluated consecutively with fresh blood added immediately after it was aspirated. The respective volume dilutions represent 0, 5%, 10%, 15% and 20% by volume of blood. Immediately after addition of blood, the tubes were inverted twice to mix and a single drop added to the test well of a Hemochron Signature Activated Blood Clotting Meter.

A similar procedure was adopted using a solution of 25,000 I.U. of Heparin, which at 5%, 10, 15% and 20% gave sample concentrations of 1,250, 2,500, 3,750 and 5,000 units per ml of test volume.

Also tested were a commercially available Catheter Locking solution, Duralock from MedComp, which contains 47% sodium citrate only, and a composition of 0.05% Methylene Blue, 0.15% Methyl Parabens, and 0.015% Propyl Parabens in 7% (0.24M) sodium citrate, being a replica of the reported formulation for Zuragen; and Taurolock from Tauropharm AG comprising 1.35% Taurolidine in 4% sodium citrate: (see Table 2). Phosphate Buffered Saline (PBS) is used as a dilution control.

It should be noted here that the Hemochron blood clotting system relies on a clot activation process which accelerates time to clot formation; whole blood without additives clots in less than 200 seconds in this apparatus. The timelines in this experiment are not directly comparable therefore with clotting times reported in Example 5 where the baseline for normal clot time is shown as 360 seconds being the observed time for normal (non-activated) clotting. It should also be noted here that the Hemochron meter goes 'out of range' at 1,000 seconds of Activated Clotting Time and more extended time recordings are not available.

Figure 3:
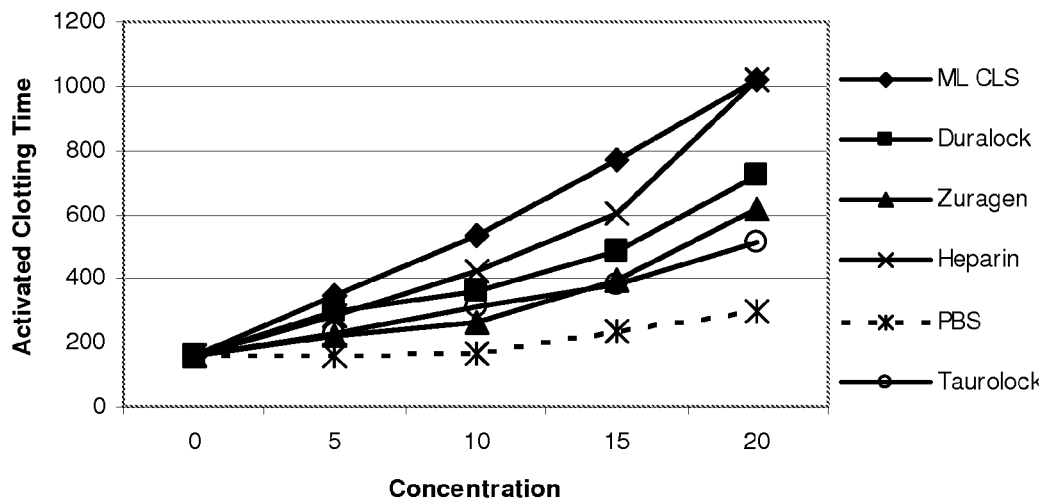
FIG. 3 illustrates anti-clotting properties of a catheter locking solution according to the invention, as described in Example 7.

The results are reported in table 11 below and illustrated in FIG. 3.

TABLE 11

Activated Blood Clotting Times for Various Catheter Locking Solutions

| | % Incorporation in whole blood | | | | |
|---|---|---|---|---|---|
| | 0% | 5% | 10% | 15% | 20% |
| ML CLS | 159 | 347 | 537 | 769 | 1018 |
| Heparin [1] | 159 | 284 | 423 | 601 | 1023 |
| Duralock | 159 | 300 | 364 | 484 | 722 |
| Zuragen | 159 | 219 | 265 | 394 | 614 |
| Taurolock | 159 | 230 | 310 | 380 | 510 |
| PBS control | 159 | 163 | 165 | 233 | 296 |

Note [1]:
Heparin concentrations range from 1,250 I.U. at 5% to 5.000 I.U. per ml at 20%

In terms of metered anti-clotting effect, the inventive product of this Example is better than 25,000 I.U. of Heparin and considerably better than Duralock, Zuragen or Taurolock. It should be noted again however, that these are 'Activated' clotting times. In practice, none of the treated samples—apart from control PBS—showed any visual sign of clotting even after several hours.

The antimicrobial effect of the formulation in this Example was tested using procedures similar to those used in Example 6, with the exception that the clot disrupting agents, heparin and streptokinase, were used to break the clots in the control untreated bloods.

18 hour Brain Heart Infusion Broth cultures of *Staphylococcus aureus*, *Streptococcus epidermidis*, *Escherichia coli* and an 18 hour culture of *Candida albicans* grown in Yeast Extract Peptone Dextrose broth were concentrated×10 by centrifugation and re-suspension in one tenth volume of supernatant.

2.5 ml aliquots of the bacterial concentrates were used to inoculate 22.5 ml volumes of freshly aspirated sheep blood, mixed and the blood dispensed as 5.0 ml, 4.75 ml, 4.5 ml, 4.25 ml and 4.0 ml volumes to Greiner centrifuge tubes containing 0, 0.25 ml, 0.5 ml, 0.75 ml and 1.0 ml volumes of the test formulation of this Example.

Figure 4:
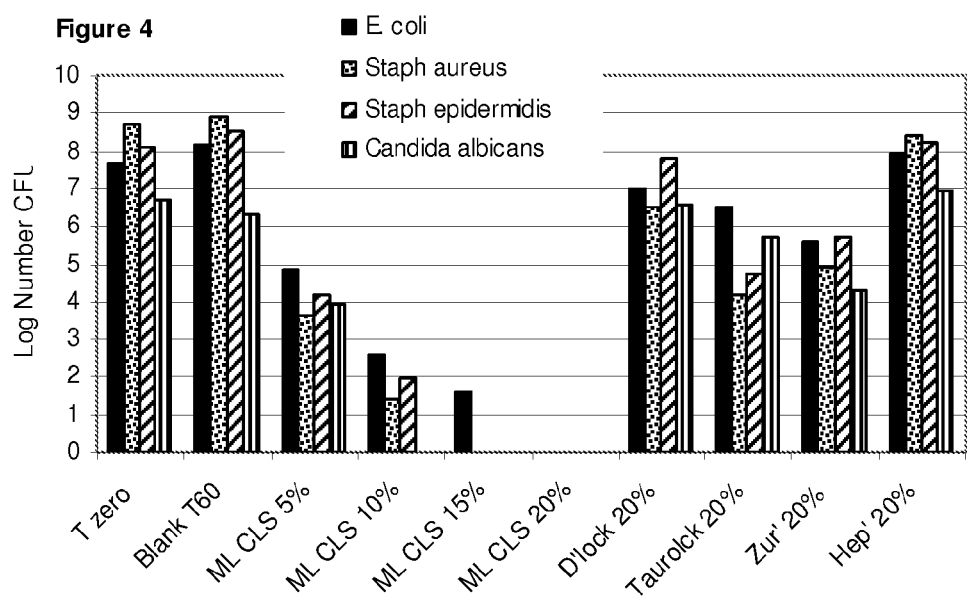
FIG. 4 illustrates comparative microbicidal potency of a catheter locking solution prepared according to the invention and compared with alternative commercial products, as described in Example 7.

The inoculated tubes were incubated for 45 minutes at 37° C. following which time, a 1.0 ml of volume of 400 I. U. heparin and 500 I. U. Streptokinase in water was added to all tubes and each was subjected to slow speed homogenization at 1,000 RPM for 2 minutes: the only visible clotting was in the control tubes. Immediately after 60 minutes had elapsed, serial dilution and plate count methods were used to assess residual viability in all samples. For comparative purposes, the same procedure was repeated with Taurolock, Duralock, Zuragen and Heparin at the maximum dose loading of 1.0 ml in 4.0 ml of blood only. The results are presented in Table 12 and illustrated in FIG. 4.

TABLE 12

Comparative Microbicidal Effect of Catheter Locking Solutions in whole blood

| | Escherichia coli | Staphylococcus aureus | Streptococcus epidermidis | Candida albicans |
|---|---|---|---|---|
| Time zero | 7.69 | 8.71 | 8.12 | 6.67 |
| Blank Time 60 min | 8.19 | 8.9 | 8.51 | 6.33 |
| ML CLS 5% | 4.83 | 3.62 | 4.17 | 3.9 |
| ML CLS 10% | 2.58 | 1.44 | 1.97 | 0 |
| ML CLS 15% | 1.62 | 0 | 0 | 0 |
| ML CLS 20% | 0 | 0 | 0 | 0 |
| Taurolock 20% | 6.53 | 4.15 | 4.72 | 5.72 |
| Duralock 20% | 6.97 | 6.49 | 7.78 | 6.54 |
| Zuragen 20% | 5.56 | 4.91 | 5.73 | 4.28 |
| Heparin 25,000 I.U. 20% | 7.92 | 8.39 | 8.22 | 6.94 |

In this test the 20% by volume ML CLS according to the invention achieved complete eradication of *E. coli* (8 logs), *Staph aureus* (8 logs), *Strep epidermidis* (8 logs) and *Candida albicans* (6 logs) in one hour in whole blood: a 5% volume achieved approximately 4 log reduction of the test inoculums in the same time. Of the four comparative preparations (Duralock, Taurolock, Zuragen or Heparin), only Zuragen and Taurolock had an appreciable microbicidal effect achieving a reduction of between 3 and 4 logs in viability of the test inoculum in one hour; Duralock appears to have a microbistatic effect while no microbial inhibition could be attributed to Heparin.

Thus, the above catheter locking solution according to the invention exhibits significantly better anti-clotting effects and much greater microbicidal effect than existing conventional products.

Example 8

Use of Membrane Lipids in Antimicrobial Surface Coating

A suitable method of applying a persistent coating of a product according to the invention involves emulsification of 1% caprylic acid in 0.8% de-lipidised lecithin prepared as described in the Methods. An equivalent volume of 100 mM sodium citrate buffer pH 4.5 is added to the emulsion to obtain a final concentration of 0.5% caprylic acid, 0.4% de-lipidised lecithin in 50 mM sodium citrate. Eight volumes of absolute ethanol are then added slowly to two volumes of the emulsion with constant vigorous stirring to make the final coating material in 80% ethanol.

In order to coat a plastic surface it is preferable to use some form of surface conditioning which may include a process known as corona discharge wherein an electrical field is generated across the surface imparting a residual charge which facilitates adhesion of the applied coat. Following corona treatment, the ethanol solution described above is sprayed on the surface and dried under forced air conditions at 60° C. Several coats may be applied to construct a layer of antimicrobial coating.

A base layer of membrane lipid may first be applied to an inert surface, and once dried and annealed it is used to 'anchor' a second layer of de-lipidised membrane lipid emulsified free fatty acid according to the invention.

In this Example an organic solvent solution of a membrane lipid is applied to the surface of a microtitre plate well, dried and fixed by heating at 60° C. followed by a further application of an aqueous suspension of caprylic acid emulsified in de-lipidised lecithin prepared as described in the Methods. The de-lipidised lecithin emulsion was dried and annealed to the first lecithin coating by heating at 60° C. for 3 hours. Plates treated with de-lipidised lecithin, without caprylic acid were used as a control and untreated plates were used to determine optimum biofilm formation.

A base layer of de-lipidised lecithin (DLL) was prepared by suspending 5% by weight DLL in 80% ethanol: water, and dispensing 100 µl aliquots of this to the test wells. Wells for determination of optimum biofilm were left untreated. The ethanol fractions were dried in a fume hood and annealed at 60° C. for one hour in an oven. 1% W/V dispersion of de-lipidised lecithin was prepared in sterile distilled water as described in Example 1, and a volume of this used to emulsify 0.25% caprylic acid. 100 µl aliquots of DLL or DLL+0.25% caprylic were transferred to DLL, pre-coated wells and dried in an oven at 60° C. for 3 hours.

A 10 hour culture of *Staphylococcus aureus* RN 4220 grown in Brain Heart Infusion broth (BHI), supplemented with 4% sodium chloride was used as inoculum. The mid log phase culture was diluted to 1% with fresh sodium chloride supplemented BHI and 200 µl of this added to the microtitre plate wells, covered and incubated.

At each sample point, 100 µl from each well was transferred to a fresh plate for assessment of growth by Optical Density at 570 nM and the plate was then decanted and washed with copious volumes of sterile distilled water, dried and annealed in an oven at 60° C.

Figure 5:
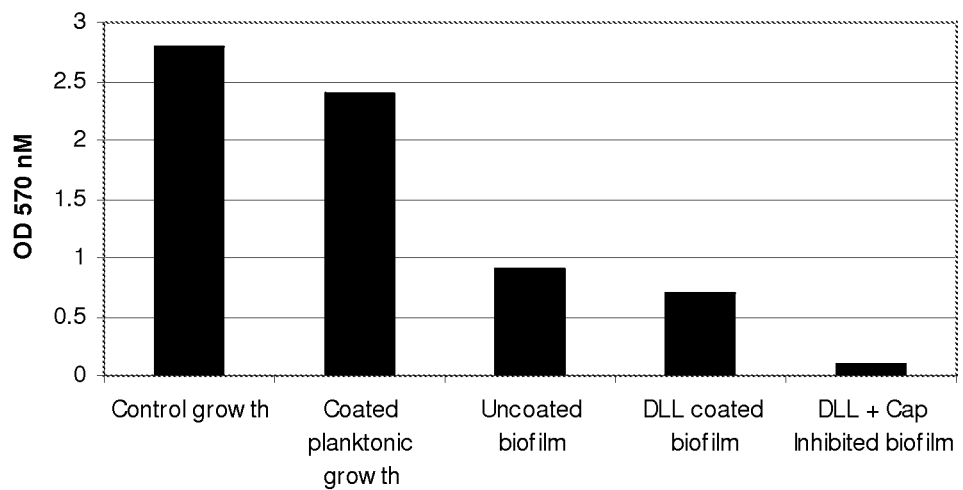
FIG. 5 illustrates the biofilm inhibitory properties of a product according to the invention, as described in Example 8.

When dry, 100 µl of 0.4% crystal violet was added to each well—including untreated controls. After 4 minutes, excess crystal was drained off, and the plates were again washed with copious volumes of water to remove excess dye and again dried with the aid of an oven at 60° C. The results are presented in table 13 and illustrated in FIG. 5.

TABLE 13

Inhibition of Biofilm Formation: 24 hour culture

|  | Optical Density 570 nM |
|---|---|
| Control growth | 2.8 |
| Coated planktonic growth | 2.4 |
| Uncoated biofilm | 0.9 |
| DLL coated biofilm | 0.7 |
| DLL + Cap Inhibited biofilm | 0.1 |

Uncoated planktonic growth is largely unaffected by the coating of inhibitory DLL+caprylic acid. Wells coated with DLL alone (DLL coated biofilm) are slightly reduced, but in comparison, wells coated with the product of this invention (DLL+Cap Inhibited Biofilm) are essentially free of any biofilm: the coating itself takes up some of the crystal violet dye which accounts for a small increase in Optical Density in the DLL+Cap wells.

Example 9

The Use of Membrane Lipids to Achieve Sustained Release of Microbicidal Free Fatty Acids In therapeutic applications considerable advantage may be gained from using combinations of membrane lipid emulsions with 'tailored' release characteristics, which facilitates sustained microbicidal effect at the epithelial surface.

In this Example individual membrane lipids were selected from each of the four classes presented in Table 1 and were the same as those used in adhesion inhibitory studies in Example 1. 0.4% Aqueous dispersions of each were prepared and 0.2% caprylic emulsified in each using procedures described in the Methods for de-lipidised lecithin (DLL). A 0.4% sample of DLL with 0.2% caprylic was also prepared. Each of the membrane lipid preparations was diluted to 50% of its volume with 200 mM sodium citrate at pH 4.5, and therefore each preparation then consisted of 0.1% caprylic acid and 0.2% membrane lipid in 100 mM sodium citrate at pH 4.5. It should be noted here that this is less than half of the microbicidal caprylic acid content of the test item used in Example 3, Table 9.

The yeast *Candida albicans* was used in this Example, and the inoculum prepared as an 18 hour YEPD broth culture as described in the Methods. The late log phase culture was centrifuged at 4,000 RPM for 5 minutes and re-suspended in one tenth volume of supernatant to concentrate×10.

Figure 6:
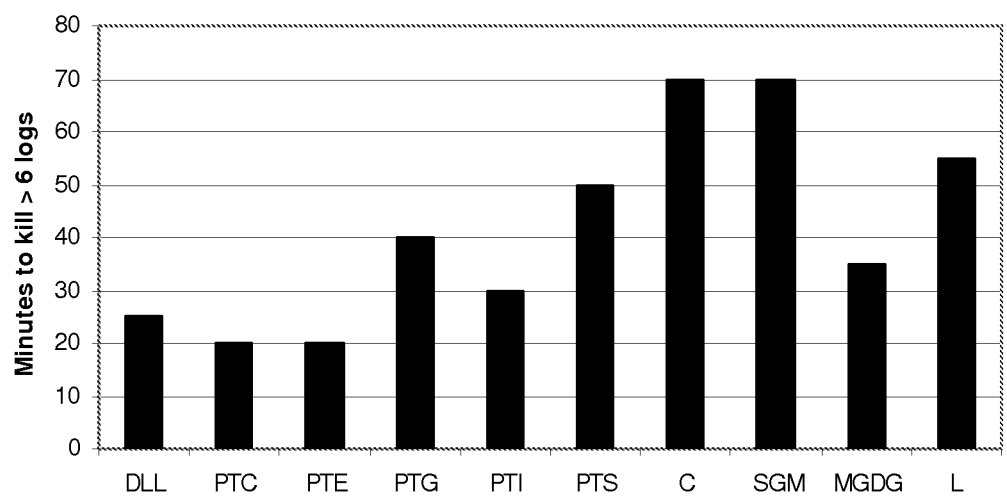
FIG. 6 illustrates the variable release of microbicidal effect achieved using different membrane lipids and caprylic acid products according to the invention, as described in Example 9.

12.0 gram samples of each test preparation were dispensed to Sterilin tubes and each of these was inoculated with 1.2 ml aliquots of concentrated yeast culture. Samples of 1.0 ml volume were withdrawn form these inoculated tubes at timed intervals over the course of one hour and added to 9.0 ml of diluting buffer containing 3% Tween 80 to neutralize. Serial dilutions and plate counting was undertaken to enumerate residual viability as described in the Methods. The results are presented in Table 14 below and illustrated in FIG. 6.

TABLE 14

Variable Release Characteristics of Membrane Lipids: Kill time for >6 logs; *Candida albicans*

| | Minutes | | | | | | | | | | | | |
|---|---|---|---|---|---|---|---|---|---|---|---|---|---|
| | 0 | 5 | 10 | 15 | 20 | 25 | 30 | 35 | 40 | 45 | 50 | 55 | 60 |
| Blank | 7.13 | 6.92 | 6.86 | 6.69 | 7.19 | 6.67 | 6.93 | 7.21 | 6.73 | 7.17 | 6.89 | 6.78 | 6.84 |
| DLL | 6.39 | 5.64 | 4.53 | 3.21 | 1.96 | 0 | | | | | | | |
| PTC | 6.5 | 4.84 | 2.57 | 1.22 | 0 | 0 | | | | | | | |
| PTE | 7.32 | 5.41 | 3.67 | 1.88 | 0 | | | | | | | | |
| PTG | 6.76 | 5.93 | 5.17 | 4.53 | 3.68 | 2.82 | 1.95 | 1.14 | 0 | | | | |
| PTI | 7.41 | 6.11 | 4.83 | 3.79 | 2.32 | 1.16 | 0 | | | | | | |

TABLE 14-continued

Variable Release Characteristics of Membrane Lipids: Kill time for >6 logs; *Candida albicans*

| | Minutes | | | | | | | | | | | | |
|---|---|---|---|---|---|---|---|---|---|---|---|---|---|
| | 0 | 5 | 10 | 15 | 20 | 25 | 30 | 35 | 40 | 45 | 50 | 55 | 60 |
| PTS | 6.8 | 6.36 | 5.85 | 5.23 | 4.53 | 3.79 | 3.13 | 2.61 | 1.88 | 1.1 | 0 | | |
| C | 7.24 | 7.28 | 6.89 | 6.54 | 6.14 | 5.96 | 5.32 | 4.97 | 4.65 | 4.29 | 3.87 | 3.74 | 3.32 |
| SGM | 6.84 | 6.55 | 6.12 | 5.85 | 5.42 | 4.87 | 4.22 | 3.76 | 3.13 | 2.79 | 2.22 | 1.84 | 1.33 |
| MGDG | 7.3 | 6.66 | 6.1 | 5.16 | 4.34 | 3.32 | 1.84 | 0 | | | | | |
| L | 7.39 | 6.45 | 5.86 | 5.34 | 4.78 | 4.21 | 3.67 | 2.98 | 2.33 | 1.74 | 1.17 | 0 | |

It is evident from the results that the slowest acting emulsions are Ceramide and Sphingomyelin followed by Lanosterol, Phosphatidylserine and Phosphatidylglycerol; the fastest acting emulsions are Phosphatidylcholine, Phosphatidylethanolamine and the combination of phospholipids in de-lipidised lecithin (DLL).

Example 10

The Use of Combinations of Antimicrobial Membrane Lipid Emulsions to Fortify Mucus and Achieve a 'Tailored' Microbicidal Effect at the Mucosal Surface Mucosal fortification involves complementary hydration, lubrication and enhanced antimicrobial effect of mucosal secretions of the eye, nose, mouth, naso-pharyngeal surfaces, the gastro-intestinal tract and the genitalia. This Example describes a preparation suitable for fortification of the mucosal secretions of the mouth and vagina and most particularly suitable for use by individuals susceptible to recurring oral and/or vaginal thrush and other common bacterial and viral infections responsive to the products of this invention.
Examples of Mucosal Fortificants:
Part A: A fast acting membrane lipid emulsion of caprylic acid (Cap) is based on 0.2% W/V Phosphatidylcholine (PTC) dispersed in sterile distilled water, hydrated and homogenized as described in the Methods and used to emulsify 0.25% W/V caprylic acid by the procedure described.
Part B: A slow acting membrane lipid emulsion of caprylic acid (Cap) is based on 0.2% Sphingomyelin (SGM), dispersed, hydrated and homogenized as described and then used to emulsify 0.25% W/V caprylic acid as described in the methods.
Part C: A 200 mM solution of citric acid is adjusted to pH 4.5 with 200 mM sodium hydroxide. A cellulose based viscosity-enhancing agent (hydroxypropylmethylcellulose, Methocel E4M from Dow Gmbh, Germany) is added at 1% W/V: the polymer is sifted in while vigorously stirring the sodium citrate solution and allowed to hydrate for 30 minutes.

A test preparation of PTC+Caprylic acid (PTC+Cap) was prepared by mixing equal amounts of Part A and Part C, yielding an emulsion of 0.125% caprylic acid with 0.1 PTC in 100 mM sodium citrate containing 0.5% W/V Methocel.

A test preparation of SGM+Caprylic acid (SGM+Cap) was prepared by mixing equal amounts of part B and Part C, yielding an emulsion of 0.125% caprylic acid with 0.1% SGM in 100 mM sodium citrate containing 0.5% W/V Methocel.

A test combination preparation comprising fast and slow acting emulsions was prepared by mixing 30% PTC+Cap with 70% SGM+Cap and combining this with an equal volume of part C (30:70 blend), The 30:70 blend is an emulsion of 0.03% caprylic acid in 0.075% PTC combined with 0.07% caprylic acid in 0.0875% SGM in 100 mM sodium citrate containing 0.5% Methocel.

The microbicidal and adhesion inhibitory properties of all three test preparations were assessed using the standard viability and adhesion inhibition assay described in the Methods. The inoculum for both assays was an 18 hour broth culture of *Candida albicans*, grown in YEPD medium and concentrated×10 by centrifugation and re-suspension in one tenth volume of supernatant.

12.0 gram samples of each test preparation were dispensed to Sterilin tubes and each of these was inoculated with 1.2 ml aliquots of concentrated yeast culture. Samples of 1.0 ml volume were withdrawn form these inoculated tubes at timed intervals over the course of one hour and added to 9.0 ml of diluting buffer containing 3% Tween 80 to neutralize. Serial dilutions and plate counting was undertaken to enumerate residual viability as described in the Methods. The results are presented in Table 15 and illustrated in FIG. 7.

TABLE 15

Mucosal Fortification: Viability of *Candida albicans* in Tailored Release Preparations

| | Minutes | | | | | | | | | | | |
|---|---|---|---|---|---|---|---|---|---|---|---|---|
| | 0 | 5 | 10 | 15 | 20 | 25 | 30 | 35 | 40 | 45 | 50 | 55 |
| Blank | 6.81 | 6.92 | 6.79 | 6.85 | 6.97 | 6.76 | 6.84 | 6.99 | 6.69 | 6.95 | 6.78 | 6.9 |
| PTC + Cap | 6.5 | 4.84 | 3.13 | 1.72 | 0 | | | | | | | |

TABLE 15-continued

Mucosal Fortification: Viability of Candida albicans in Tailored Release Preparations

| | Minutes | | | | | | | | | | | |
|---|---|---|---|---|---|---|---|---|---|---|---|---|
| | 0 | 5 | 10 | 15 | 20 | 25 | 30 | 35 | 40 | 45 | 50 | 55 |
| SGM + Cap | 6.84 | 6.55 | 6.12 | 5.85 | 5.42 | 4.87 | 4.22 | 3.76 | 3.13 | 2.79 | 2.22 | 1.84 |
| 30:70 blend | 6.73 | 5.21 | 4.14 | 3.56 | 3.12 | 2.8 | 2.42 | 2.16 | 1.89 | 1.55 | 1.33 | 0.89 |

The fast acting PTC+Cap behaved as expected reducing viability to zero detectable cells in 20 minutes. The slow acting SGM+Cap was also as expected with viability being reduced by 5 logs in 55 minutes. The combination 30:70 blend gives a good example of a 'tailored release' profile, viability was reduced by more than 2 logs in 10 minutes, a rate which paralleled the fast acting PTC+Cap, thereafter the microbicidal rate slowed considerably, and approximated to that of the slow acting SGM+Cap. The blend however had achieved 1 log greater reduction in viability at 55 minutes compared to SGM+Cap alone.

Assessment of adhesion inhibitory properties of the three test preparations was undertaken using the Buccal Epithelial Cell model described in the Methods and used in Example 1. For comparison, preparations of the two membrane lipids, PTC and SGM, at 0.1% in 100 mM sodium citrate buffer pH 4.5 with 0.5% Methocel were also prepared and included in the test procedure.

Figure 8:
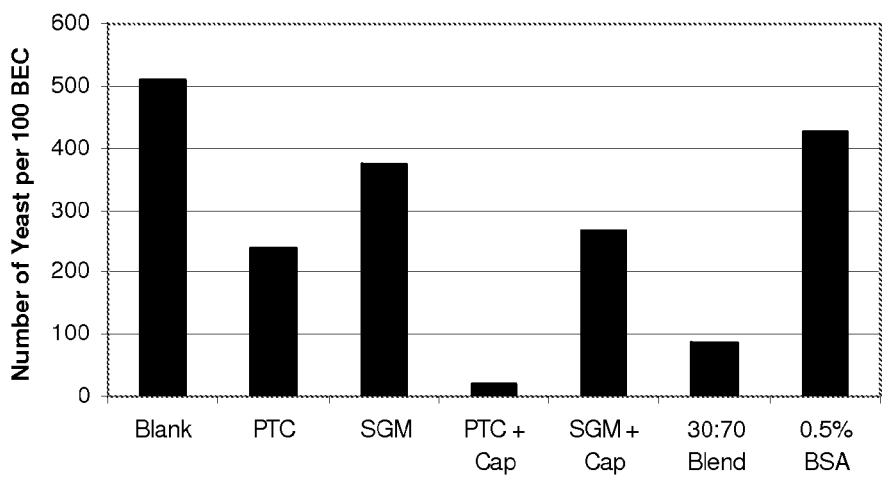
FIG. 8 illustrates inhibition of adhesion of *Candida albicans* by tailored release products according to the invention, as described in Example 10.

Washed yeast cell pellets were re-suspended in 2.5 ml volumes of the test preparations (PTC, PTC+Cap, SGM, SGM+Cap, 30:70 blend described above and BSA blank). 100 mM sodium citrate at pH 4.5 was used for determination of control adhesion. After 10 minutes pre-exposure, the yeast suspensions were used to re-suspend washed Buccal Epithelial Cell pellets which had been harvested and prepared as described in the Methods. The combined yeast and Buccal Epithelial cell in test, blank or control were incubated with gentle agitation for 60 minutes at 37° C., after which direct microscopic counts using a Hemocytometer slide were used to enumerate the numbers of yeast adhering to 100 Buccal Epithelial cells: The results are presented in Table 16 and illustrated in FIG. 8.

TABLE 16

Mucosal fortification: Inhibition of Adhesion in Tailored release Preparations: Candida albicans to Buccal Epithelial Cell

| | Count/ 100 BEC | % Adhesion | % Inhibition |
|---|---|---|---|
| Blank | 509 | 100 | 0 |
| PTC | 239 | 47 | 53 |
| SGM | 374 | 73 | 27 |
| PTC + Cap | 20 | 4 | 96 |
| SGM + Cap | 266 | 52 | 48 |
| 30:70 Blend | 88 | 17 | 83 |
| 0.5% BSA | 425 | 83 | 17 |

The adhesion inhibitory properties of 0.1% PTC on its own and with 0.125% caprylic acid are considerably better than equivalent preparations of SGM: as might be expected the 30:70 blend lies midway between the two.

From the data in Table 16 it is also evident that the emulsified fatty acid has a synergistic effect on the adhesion inhibitory properties of the membrane lipid. The percentage reduction in adhesion achieved with PTC alone (53%), is reduced by a further 43% in combination with caprylic acid.

Figure 7:
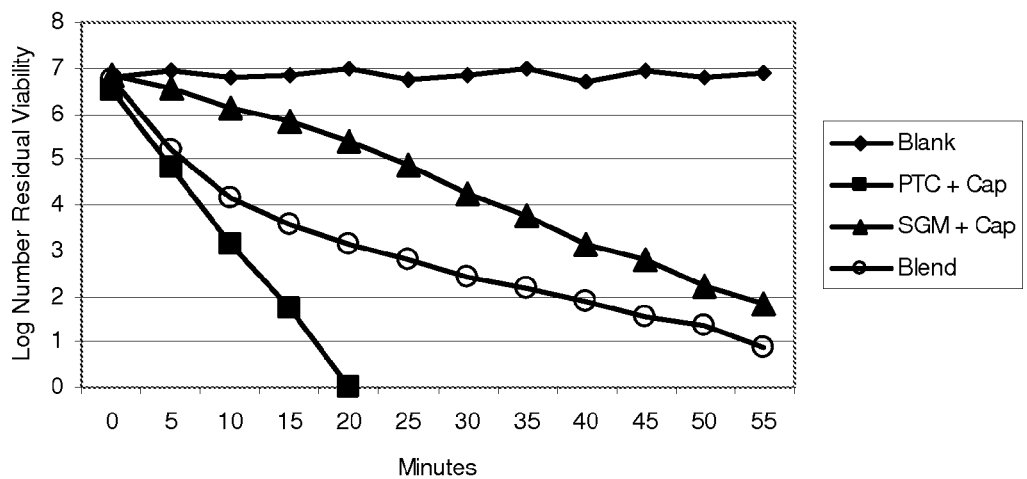
FIG. 7 illustrates reduction in viability of *Candida albicans* in response to tailored release characteristics of products according to the invention, as described in Example 10.

It should be noted that according to the viability data in Table 16 and as illustrated in FIG. 7, none of the yeast cells in PTC+Cap is viable after 20 minutes exposure, and approximately 50% to 60% of those in the other two samples are dead. Under the microscope however, yeast cells appear to be intact and while greatly reduced there are still a few apparent that are adhering to Buccal Epithelial cells, suggesting that dead cells are capable of adhesion and biofilm formation.

Example 11

The Use of Membrane Lipids in Skin Antisepsis and Prevention of Cross Contamination in Hospitals and Patient Care Establishments Methods of evaluating skin antiseptic agents in wash and gel formulations are well established and are fully described in the official procedures of the EU for ISO Certification under EN 1500 (hand gel) and EN 1499 (liquid soap).

In this Example, the relatively non-pathogenic *Escherichia coli* K12 NCTC 10538 was used (The National Collections of Industrial and Marine Bacteria Ltd, UK: Catalogue of Type Strains ISBN No 0 9510269 3 3). The bacterium is routinely cultured and maintained on tryptone soya agar or broth (TSB), which may be acquired commercially from Oxoid, UK and has the following constituents: 1.5% W/W tryptone (pancreatic digest of casein), 0.5% W/W peptone (papaic digest of soybean meal), 0.5% W/W sodium chloride, and agar at 1.5% WAN when required as a solid medium.

Prior to the test volunteers wash their hands with a mild non-antiseptic soap; a suitable product is E45 Emollient Wash Cream from Boots Healthcare, UK. After washing and drying, the hands are dipped into a 2 liter beaker containing 1 liter of 24 hour culture of *E. coli* grown in TSB and containing not less than $2\times10^8$ viable cells per ml as confirmed by serial dilution and plate counting. Both hands are immersed in the contaminating suspension up to the mid-metacarpals and held there for 5 seconds, and then removed. Excess contaminating fluid is allowed to run-off and then the hands are air dried in the horizontal position for 3 minutes.

To ensure adequate contamination and to establish a pre-value for enumerating reduction, the hands are sampled by dipping the tips of the fingers and thumb of each hand into 10 ml of sterile PBS in a Petri-dish, and rubbed against the base of the plate for 1 minute. After sampling, the hands are treated with either the product of this invention or Spirigel; 4 ml of either preparation is applied to the hands and manipulated over the entire surface area of both hands. The hands are then rinsed under clean (potable) running water, which is lukewarm at approximately 37° C. for a timed period of 20 seconds. After rinsing, the hands are held in an upright position while an assistant dries the palms and wrists with a paper towel. The finger tips and thumb are then sampled by immersion in 10 ml of PBS as described above.

Immediately after sampling, prior to or after washing, 1 ml of the sampling fluid was aseptically transferred to and spread on the surface of a TSB agar plate and another 1 ml is transferred aseptically to 9 ml of sterile PBS and mixed and the process of serial dilution and plate counting proceeds as described previously.

A test preparation of the product of this invention was prepared, being a combination of caprylic acid in phosphatidyl choline at 30% and caprylic acid in sphingomyelin at 70% prepared as described in the Methods. In this Example the membrane lipids were prepared as 1% concentrates with 1% caprylic acid and blended at 30:70 ratio.

A viscosity-enhancing agent is employed to improve the rheology of the test preparation. In this case a Carbopol co-polymer, Pemulen TR-1 from Noveon Inc, Cleveland Ohio was used at 0.45%. The polymer was added to a volume of absolute ethanol equivalent to 70% of final preparation volume and allowed to disperse therein for 30 minutes. A 30% volume of 30:70 blend of the product of this invention as described above was then added to the ethanol and polymer with constant stirring to facilitate rapid dispersion.

The Final Test Product Contains:
0.045% Caprylic acid in 0.045% Phosphatidylcholine: 0.105% Caprylic acid in 0.105% Sphingomyelin: 0.45% Carbopol polymer; 29.25% water; 70% ethanol.

Spirigel is reported to contain 70% ethanol, 30% water and an unknown amount of an unknown viscosity-enhancing agent.

In this Example both test product and Spirigel were used immediately after experimental contamination of volunteers' hands to evaluate de-contamination, and both were used on experimentally re-contaminated hands 10 minutes after application of Spirigel and test preparation according to the invention; the results are presented in Table 17.

TABLE 17

Persistent Effect of tailored release membrane lipids in skin antisepsis

|  | Spirigel | Test item |
|---|---|---|
| Pre-treatment contamination | 6.42 | 6.69 |
| Post treatment contamination, i.e. residual viability | 3.23 (−3.19) | 3.42 (−3.27) |
| Pre-application 10 min pre-contamination (treatment 10 min pre-contamination) | Not Applicable | Not Applicable |
| Contamination: 10 min post treatment | 6.42 | 6.59 |
| Contamination: 10 min Post application, i.e. viable cells recovered for contamination 10 mins post application | 5.97 | 2.67 (−3.3) |

As might be anticipated from the alcohol content, when used immediately after contamination both products achieved greater than 3 log reductions of the applied contamination. When used on hands 10 minutes prior to contamination however the alcohol content of both products had evaporated by the time the contamination was applied, and the results show that Spirigel had no significant residual effect (0.45 log reduction). The persistent nature of the membrane lipid emulsion of fatty acid was still present on the hands in the test item, and achieved greater than 3 log reduction. Spirigel has an immediate but no persistent antimicrobial effect, while the test item according to this invention is both immediate and persistent microbicidal effects.

Example 12

Use of Membrane Lipid Emulsions in Wound Care

To illustrate the potential utility of the product of this invention in wound care an ex-vivo model employing freshly slaughtered sections of beef brisket is used. Brisket has an optimal distribution of lean muscle, fat and collagen, and is consequently considered to be representative of all potentially infected wound surfaces. Brisket sections are excised immediately post slaughter, without chilling and with the external fascia membrane intact, these are divided under aseptic conditions into cubes of approximately 1 cm square. Prepared cubes are 'infected' by submerging them in late log phase cultures of bacteria for one minute, dried and suspended in a 37° C. environment for one hour to facilitate bacterial adherence and colonization of the meat surfaces.

A suitable example of a wound care formulation is the "standard formulation" of this invention (containing 0.5% caprylic acid in 0.4% DLL) diluted 1:1 in 200 mM sodium citrate buffer at pH 4.5, which then consists of 0.25% caprylic acid in 0.2% DLL in 100 mM sodium citrate buffer at pH4.5

Test sections of infected meat are treated by spraying the wound care formulation directly onto the infected surface and evaluating the test samples for residual bio-burden at predetermined exposure times. Infection and its eradication are confirmed by mechanical maceration of treated and untreated sections in sterile phosphate buffered saline (PBS) and enumeration of the bio-burden by standard microbiological serial dilution and plate counting techniques.

Figure 9:
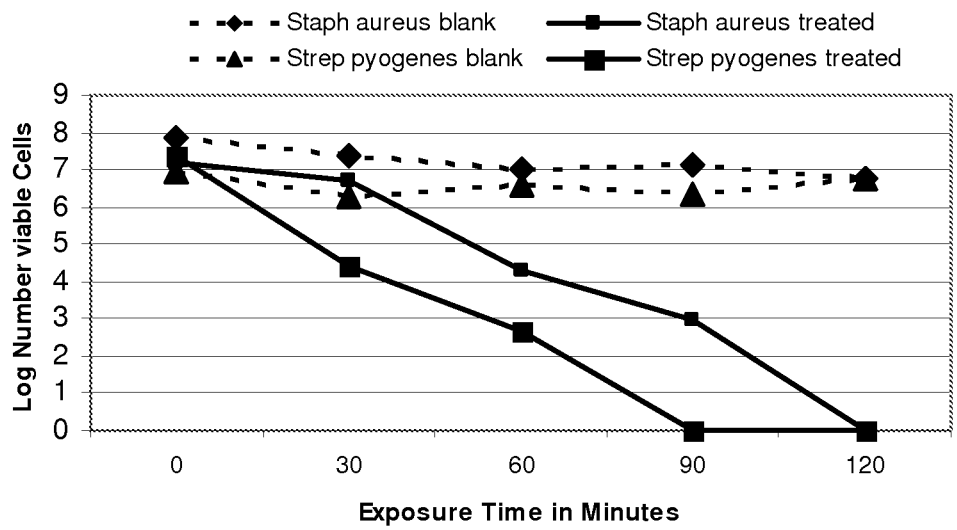
FIG. 9 illustrates the eradication of *Staphylococcus aureus* and *Streptococcus pyogenes* from an ex-vivo wound model, as described in Example 12.

Typical results are presented in FIG. 9, where greater than 7 logs of the common wound infecting bacteria, *Staphylococcus aureus* and *Streptococcus pyogenes* are shown to be eradicated in less than 120 minutes. It should be appreciated that the rate of kill on a fissured surface such as a wound is extended due to the nature of the surface and the time required for the formulation to permeate to the seat of the infection.

Figure 10:
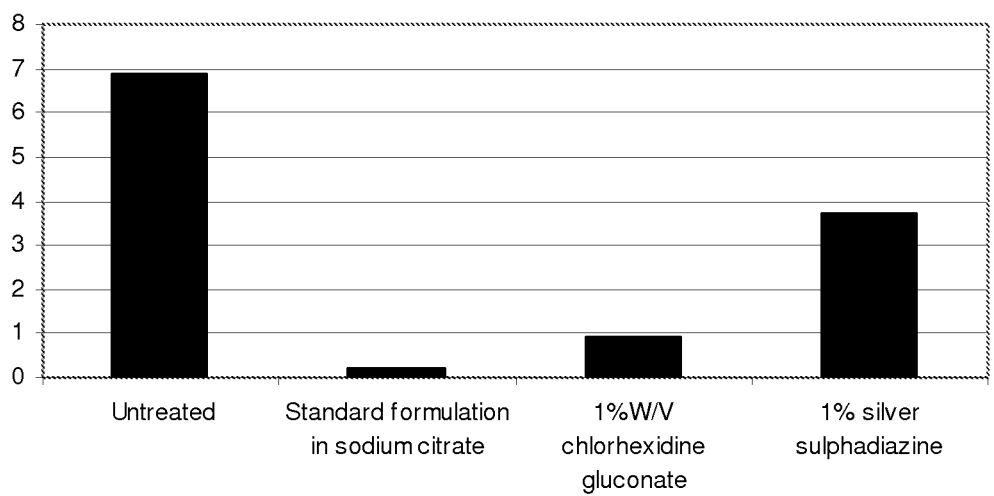
FIG. 10 is a comparison of the ex-vivo efficacy of a product of the invention in sodium citrate with conventional wound care antimicrobials, chlorhexidine and silver sulfadiazine, as described in Example 12.

A comparison of the relative potency of the standard formulation in citrate buffer as above with the alternative and commonly used antimicrobials, chlorhexidine gluconate and silver sulphadiazine is presented in FIG. 10. At 100 minutes exposure the product of this invention has virtually eradicated 7 logs of *Staphylococcus aureus:* 1 log remains under chlorhexidine treatment and 3.5 logs with silver sulphadiazine.

Example 13

The Surgical Use of Membrane Lipids in Prevention and Disruption of Biofilm

*Staphylococcus aureus* RN4220 is noted for its ability to form tenacious biofilm under laboratory conditions when stress cultured in the presence of sodium chloride. The organism was cultured to mid log phase (10 hours) in Brain Heart Infusion broth and 20 micro-liter volumes used to inoculate wells of a 96 well microtitre plate containing 180 μl of BHI supplemented with 4% sodium chloride. When incubated at 37° C. under these conditions for 6 hours an appreciable biofilm is formed at the base of each well. The biofilm is quantified by decanting the culture and washing the wells with sterile distilled water, after which the plates are dried and stained with 0.4% crystal violet, re-washed and dried; the Optical Density of the stained biofilm is measured at 570 nm.

From previous Examples it will be clear that incorporation of the membrane lipid emulsified product of this invention will have a microbicidal effect, preventing growth and biofilm formation. As illustrated here where biofilm already exists, however, contact with an emulsion of membrane lipid and free fatty acid will effectively kill all viable bacteria in the biofilm and disrupt the film itself.

Assessment of reduction of viability of an established biofilm prepared as described above was achieved by incorporating Alamar Blue at 10% by volume in fresh BHI broth and re-charging the wells of a 96 well microtitre plate with pre-formed biofilm. Alamar Blue is a redox indicator from Invitrogen Ltd, Paisley, UK. It imparts a deep blue color to the media, and when reduced by microbial metabolic activity the color changes from non-fluorescent blue to a highly fluorescent red; absorbance and emerging fluorescence may be measured at 570 nm and 600 nm.

Microtitre plate wells containing pre-formed biofilm were treated with the membrane lipid CLS (ML CLS) used in Example 7 and similar wells were also treated with Zuragen, Duralock and Taurosept for time periods ranging from zero to 60 minutes. At the end of each exposure period, the plates were decanted and washed once with phosphate buffered saline containing 3% Tween 80 and twice with sterile distilled water. 200 µl of BHI containing 10% Alamar Blue was added to the wells and the plates incubated for 60 minutes. There was no detectable color change in any of the wells treated with the membrane lipid CLS of this invention indicating complete eradication of viability within the biofilm in less than one hour. All of the wells treated with Zuragen, Duralock or Taurosept had changed from blue to red demonstrating little or no reduction in viability in the established biofilm.

The efficacy of the membrane lipid CLS of this invention, and the comparable ineffectiveness of the other three formulations in reducing the actual amount of pre-formed biofilm may be demonstrated using similar procedures.

Figure 11:
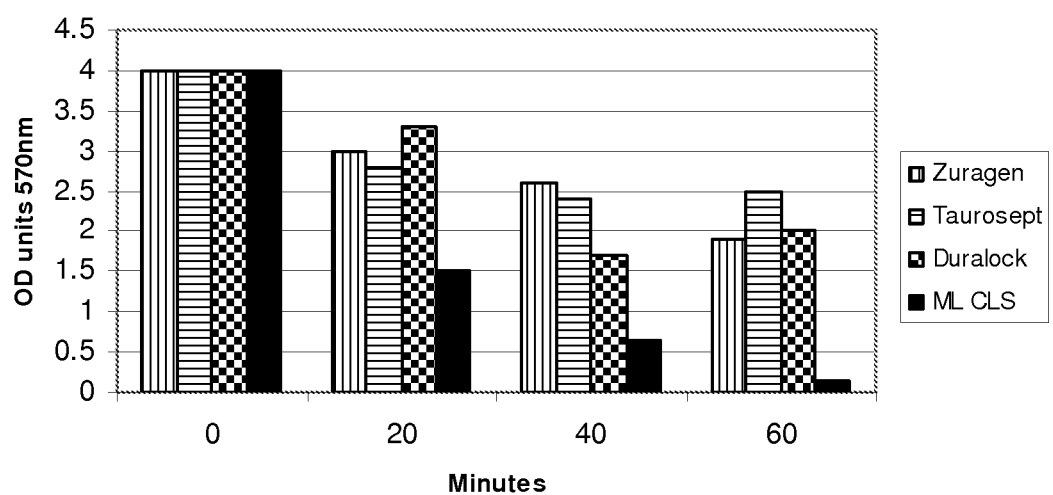
FIG. 11 illustrates comparative eradication of established biofilm and the superior efficacy of a product of the invention over existing commercially available catheter locking solutions, as described in Example 13.

Microtitre plate wells containing pre-formed biofilm were treated with the four formulations for time periods from zero to 60 minutes, decanted and washed as described previously. The treated plates were dried and stained with 0.4% crystal violet, dried and the intensity of stain being a measure of residual biofilm was recorded at 570 nm. The results are illustrated in FIG. 11 wherein it is evident that although some reduction in biofilm was achieved with Zuragen, Duralock and Taurosept, it is inconsequential in comparison to the near total eradication of biofilm achieved with the membrane lipid CLS (ML CLS) of this invention.

Example 14

Comparative Adhesion Inhibitory Properties

De-lipidised lecithin is a more potent adhesion inhibitory substance compared to milk serum apo-proteins in WO 03/018049, wherein the apo-proteins are generated by lipase hydrolysis of whey proteins. For adhesion inhibitory comparison, a whey protein hydrolysate was prepared as described in WO 03/018049 using Carbelac 80 whey protein concentrate. A whey protein isolate (Provon 190 from Glanbia PLC) was also tested contemporaneously. For full comparison purposes a formulation of 0.5% W/V caprylic acid in 0.4% W/V de-lipidised lecithin was prepared in 100 mM sodium citrate pH 4.5 as described in the Methods and included in the test sequence. All test items were dispersed in 100 mM sodium lactate buffer at pH 4.5. The results are presented in Table 18 below.

TABLE 18

| *Candida albicans* per 100 Buccal Epithelial Cells | | | | | |
|---|---|---|---|---|---|
| | 0 mg/ml | 2.5 mg/ml | 5.0 mg/ml | 10 mg/ml | 15 mg/ml | % inhibition at 5 mg/ml |
| Carbelac 80 | 483 | 395 | 320 | 260 | 189 | 33 |
| Provon 190 | 514 | 313 | 277 | 113 | 53 | 46 |
| Lipase digest of Carbelac 80 | 491 | 330 | 154 | 48 | 0 | 68 |
| De-lipidised lecithin (DLL) | 504 | 130 | 33 | 0 | 0 | 93 |
| 0.5% Caprylic in 0.4% DLL | 517 | 46 | 0 | 0 | 0 | 100 |

While de-lipidised lecithin on its own is significantly better than the three dairy based preparation, the emulsified combination of de-lipidised lecithin and caprylic acid is the most potent.

Example 15

Comparative Microbicidal Effect

The MIC by agar dilution technique is also used here to demonstrate the superior potency of the "standard formulation" described hereinabove over the product disclosed in WO2009/072097 comprising a blend of free fatty acids emulsified in the whey protein isolate, Provon 190 from Glanbia PLC. The product of WO2009/072097 contains 28% by weight of free fatty acid blend, while the standard formulation of this inventions contains just 0.5% by weight. In order to make a suitable comparison between the two products the product of WO2009/072097 was diluted by 5/28 in sterile distilled water to obtain a dispersion comprising 5.0% free fatty acid which was then diluted further and used to prepare agar plates ranging from 1.0% free fatty acid to 0.5%, 0.4%, 0.3%, 0.2%, 0.1%, 0.075%, 0.05% and 0.025% (of fatty acid content).

For further comparison an emulsion was constructed using 0.5% caprylic acid in 0.4% Provon 190, using the emulsification agent from WO2009/072097 instead of de-lipidised lecithin. The results are shown in Table 19 below.

TABLE 19

Comparative MIC values

| Test organism | Product of WO/2009/ 072097 | 0.5% Caprylic in 0.4% Provon 190 | Formulation of invention containing 0.5% caprylic acid in 0.4% DLL |
|---|---|---|---|
| Staph aureus RN4220 | >0.4% | >0.7% | >0.1% |
| Staph epidermidis NCTC 11047 | >0.4% | >0.7% | >0.1% |
| Strep pyogenes NCTC 8198 | >0.4% | >0.7% | >0.075% |
| Strep faecalis NCTC 12697 | >0.4% | >0.7% | >0.075% |
| E. coli ATCC 11698 | >1.0% | >1.0% | >0.4% |
| Salmonella typhimurium NCTC 74 | >0.8% | >0.8% | >0.3% |
| Pseudomonas aeruginosa ATCC 27853 | >1.0% | >1.0% | >0.5% |
| Pseudomonas fluorescens NCTC 10038 | >1.0% | >1.0% | >0.5% |
| Candida albicans C.I. | >0.4% | >0.7% | >0.075% |
| Candida glabrata NCPF 8750 | >0.4% | >0.7% | >0.1% |

For the two *Staphylococci*, the two *Streptococci* and the *Candida* sp, the measured MIC for the standard formulation is one quarter or less than that of the product of WO2009/072097, indicating a four times greater potency. In the case of the two *Pseudomonas* sp, *E. coli* and *Salmonella*, the measured MIC is one half to one third less than the product of WO2009/072097 again clearly demonstrating significantly greater potency. The measured MIC's for the emulsion of caprylic acid in Provon 190 are significantly greater (significantly less potent) than the standard formulation of this invention.

Example 16

Comparative Microbicidal and Adhesion Inhibitory Effect of Different Free Fatty Acids in Both Emulsified and Free Form Fatty acids in free form (not emulsified) have relatively little microbicidal effect primarily because of their insolubility in aqueous medium. Emulsification in membrane lipids as described herein expands the relative surface area of the fatty acid and facilitates its dispersal in aqueous medium. The membrane lipid emulsification agent also facilitates contact and transfer of the fatty acid to a microbial cell surface. As illustrated in previous Examples, variable lipophylicity between different membrane lipids affects the rate of microbicidal effect. In general, membrane lipids are superior emulsification agents, exhibiting superior microbicidal effect as demonstrated in Example 15. As demonstrated here the superior potency of membrane lipid emulsified free fatty acid extends across a range of microbicidal fatty acids.

Seven separate emulsions of seven different free fatty acids at 0.5% W/V were prepared in 0.4% W/V de-lipidised lecithin as described in the methods. Emulsions were prepared at temperatures above the melting points of the individual free fatty acids: caproic, caprylic and pelargonic at room temperature (20° C.); capric and undecylenic acid were prepared at 37° C., lauric acid was emulsified at 50° C. and myristic at 60° C. A blend of 50% caproic and 50% lauric acid has a melting point of less than 28° C. as does a blend of 40% lauric acid in oil of lemon balm, and these were emulsified at 37° C.

The comparative microbicidal effect of each individual fatty acid and blend thereof in free non-emulsified form and emulsified in de-lipidised lecithin was evaluated using the microbicidal suspension test described in the methods. Evaluation of the microbicidal effect of free non-emulsified fatty acids is frustrated by their insolubility. Inclusion of the non-emulsified form was considered necessary to illustrate the exponential increase in potency in the emulsified form. Each free fatty acid was prepared at 0.5% W/V in water and agitated vigorously to disperse followed by immediate pipetting of 1.0 ml aliquots to test containers, prior to inoculation with the test organism. The test organism was *Staphylococcus aureus* RN 4220 grown to late log phase on Brain Heart Infusion Broth.

The results are presented in Table 20 below.

TABLE 20

Comparative Microbicidal Effect
Free fatty acids or blends thereof at 0.5% W/V non-emulsified in the test and at 0.5% W/V emulsified in 0.4% W/V de-lipidised lecithin in the test.

| | Exposure Time in Seconds at 37° C. | | | | | | |
|---|---|---|---|---|---|---|---|
| Fatty acid or blend | 0 | 60 | 120 | 180 | 240 | 300 | 360 |
| Free caproic acid | 7.87 | 7.17 | 6.82 | 7.57 | 6.93 | 6.47 | 6.73 |
| Emulsified caproic acid | 7.87 | 6.21 | 4.89 | 2.53 | 0 | 0 | 0 |
| Free caprylic acid | 6.94 | 6.79 | 6.83 | 6.21 | 6.33 | 5.89 | 6.17 |
| Emulsified caprylic acid | 6.94 | 5.32 | 3.71 | 0 | 0 | 0 | 0 |
| Free pelargonic acid | 6.94 | 6.55 | 6.31 | 5.96 | 5.67 | 5.83 | 5.27 |
| Emulsified pelargonic acid | 6.94 | 4.63 | 2.99 | 1.81 | 0 | 0 | 0 |
| Free capric acid | 6.94 | 6.32 | 6.48 | 6.73 | 6.36 | 5.97 | 6.11 |
| Emulsified capric acid | 6.94 | 4.79 | 3.44 | 2.19 | 0 | | |
| Free undecylenic acid | 7.87 | 7.19 | 6.99 | 6.57 | 6.83 | 6.67 | 6.31 |
| Emulsified undecylenic acid | 7.87 | 4.97 | 2.69 | 0 | 0 | 0 | 0 |
| Free lauric acid | 7.87 | 7.35 | 7.77 | 7.41 | 7.98 | 7.23 | 7.65 |
| Emulsified lauric acid | 7.87 | 5.79 | 4.63 | 3.86 | 2.55 | 0 | 0 |
| Free myristic acid | 7.38 | 7.27 | 7.84 | 6.93 | 7.11 | 6.26 | 6.84 |
| Emulsified myristic | 7.38 | 6.46 | 5.81 | 5.21 | 4.98 | 3.69 | 2.99 |
| Free lauric caproic 50:50 | 7.38 | 6.99 | 7.18 | 6.74 | 6.37 | 6.95 | 6.81 |
| Emulsified Lauric: caproic | 7.38 | 6.76 | 5.32 | 3.17 | 2.98 | 0 | 0 |
| Free 40% lauric in oil of lemon balm | 7.38 | 7.21 | 7.76 | 7.39 | 6.95 | 6.87 | 6.49 |
| Emulsified 40% Lauric in Oil of Lemon Balm | 7.38 | 5.92 | 3.13 | 2.77 | 0 | 0 | 0 |
| De-lipidised Lecithin 0.4% W/V | 7.33 | 7.92 | 7.41 | 6.83 | 7.14 | 7.66 | 6.95 |

Blank determinations were conducted in all assays by suspending the inoculum in phosphate buffered saline at 37° C. and no reduction in inoculum viability was detected over the six minute exposure period in any test sequence.

Free fatty acids in non-emulsified form achieve at best 1 log reduction in viability over the test period of 6 minutes. The membrane lipid emulsification agent (de-lipidised lecithin) equally exerts little or no microbicidal effect. In comparison, with the exception of emulsified myristic acid, equivalent weight emulsions of all other fatty acids and blends thereof in de-lipidised lecithin reduce residual viability in a test inoculum of 6.94 to 7.87 logs to zero in less than 4 minutes.

Neither free fatty acids on their own nor the de-lipidised membrane lipid on its own have any detectable microbicidal effect within the time-frame of this test. An emulsified combination of the two enables the microbicidal effect of the fatty acid synergistically.

The same test items used in microbicidal evaluation above were also tested for their adhesion inhibitory properties using the Buccal Epithelial Cell assay described in the Methods.

TABLE 21

Comparative Adhesion Inhibitory Effect
Free fatty acids or blends thereof at 0.5% W/V non-emulsified in the test
and at 0.5% W/V emulsified in 0.4% W/V de-lipidised lecithin in the test.

| Fatty acid or blend | Blank Count/ 100 BEC | Test Count/ 100 BEC | % Adhesion | % Inhibition |
|---|---|---|---|---|
| Free caproic acid | 429 | 380 | 89 | 11 |
| Emulsified caproic acid | 503 | 0 | 0 | 100 |
| Free caprylic acid | 429 | 400 | 93 | 7 |
| Emulsified caprylic acid | 503 | 0 | 0 | 100 |
| Free pelargonic acid | 429 | 360 | 84 | 16 |
| Emulsified pelargonic acid | 503 | 2 | 0.3 | 99.7 |
| Free capric acid | 429 | 386 | 90 | 10 |
| Emulsified capric acid | 503 | 0 | 0 | 100 |
| Free undecylenic acid | 521 | 448 | 86 | 14 |
| Emulsified undecylenic | 508 | 0 | 0 | 100 |
| Free lauric acid | 474 | 450 | 95 | 5 |
| Emulsified lauric acid | 508 | 56 | 11 | 89 |
| Free myristic acid | 474 | 436 | 92 | 8 |
| Emulsified myristic | 508 | 68 | 13 | 87 |
| Free lauric caproic 50:50 | 474 | 450 | 95 | 5 |
| Emulsified Lauric:caproic | 508 | 0 | 0 | 100 |
| Free 40% lauric in oil of lemon balm | 526 | 460 | 87 | 13 |
| Emulsified 40% Lauric in Oil of Lemon Balm | 526 | 0 | 0 | 100 |
| De-lipidised Lecithin 0.4% W/V | 497 | 96 | 19 | 81 |

De-lipidised lecithin on its own in the test achieves 81% inhibition of adhesion. Emulsions of caproic, caprylic, pelargonic, capric and undecylenic achieve greater than 99% inhibition, and emulsions of lauric and myristic achieve greater than 86% inhibition. All non-emulsified free fatty acids achieve less than 17% inhibition. The adhesion inhibitory effect of caprylic acid for example is amplified by a factor of 14 in emulsified form.

At the concentrations of test item used in Table 21, the adhesion inhibitory effect is essentially swamped by the intrinsic microbicidal effect. It has been demonstrated that the majority of microbial cells will be dead as a result of exposure to the microbicidal effect of the emulsified fatty acid, and it must be assumed that this will influence adhesion.

A more appropriate measure of the amplified adhesion inhibitory effect attributable to emulsions vs free acid or non-emulsified membrane lipids may be obtained using a concentration below the Minimum Inhibitory Concentration (MIC) of the emulsified free fatty acid. The MIC of caprylic acid in the formulation of this invention is greater than 0.1%.

A formulation of 0.5% caprylic in 0.4% de-lipidised lecithin (as used above) is diluted by a factor of 5 in sterile distilled water to achieve a concentration of 0.1% caprylic in 0.08% de-lipidised lecithin and further diluted by half to achieve 0.05% caprylic in 0.04% DLL. These dilutions together with the same concentrations of DLL and non-emulsified free caprylic acid were tested in the Buccal Epithelial Cell assay as above. The results are presented in Table 22.

TABLE 22

Low Dose Adhesion Inhibitory Effect
Caprylic acid at 0.1% W/V and 0.05% W/V non-emulsified in
the test and at 0.1% W/V and 0.05% W/V emulsified in 0.08%
W/V and 0.04%% W/V DLL respectively in the test, together
with 0.08% and 0.04% non-emulsified DLL.

| | Blank Count/ 100 BEC | Test Count/ 100 BEC | % Adhesion | % inhibition |
|---|---|---|---|---|
| Free caprylic acid 0.1% | 489 | 466 | 95 | 5 |
| Free caprylic acid 0.05% | 487 | 459 | 94 | 6 |
| DLL 0.08% | 533 | 421 | 85 | 15 |
| DLL 0.04% | 509 | 453 | 87 | 13 |
| 0.1% caprylic in 0.08% DLL | 499 | 255 | 51 | 49 |
| 0.05% caprylic in 0.04% DLL | 513 | 303 | 59 | 41 |

As illustrated in Table 22, the addition of caprylic acid at concentrations below its MIC (0.1% and 0.05%) amplifies the adhesion inhibitory effect of 0.08% DLL and 0.04% DLL by more than a factor of three in both cases.

Example 17

Reduction of Antagonistic Effect on Mammalian Cells

Mammalian cell membranes are susceptible to disruption by free fatty acids in a manner not dissimilar to their effect on microbial cell membranes. The effect is not classical cell toxicity as it relates to superficial cell surface damage and not interference with metabolic process or nucleic acid replication. It is ameliorated significantly by body fluids in vivo. Protection against mammalian cell membrane damage can be enhanced by adding additional amounts of free membrane lipid to a membrane lipid emulsion of a free fatty acid. The protective effect is not confined to the use of membrane lipids. As illustrated here, milk serum whey protein isolate also serves as a suitable, although not optimal barrier against mammalian cell damage.

The test item is an emulsion of 0.5% caprylic acid in 0.4% de-lipidised lecithin prepared as described in the Methods, and combined with an equal volume of 200 mM sodium citrate at pH 4.5 also prepared as described in the Methods. Dispersions of 0.4% and 0.8% de-lipidised lecithin were prepared in 200 mM sodium citrate at pH 4.5, and combined in equal volumes with aliquots of the emulsion of caprylic acid in de-lipidised lecithin to achieve emulsions of 0.25% caprylic acid in 0.2% de-lipidised lecithin suspended in an aqueous solution of 100 mM sodium citrate at pH 4.5 in which further amounts of either 0.2% or 0.4% de-lipidised lecithin were dispersed, these are described as Test+0.2% DLL or Test+0.4% DLL Similar suspensions of the same emulsion were prepared in sodium citrate dispersions of a Whey Protein Isolate (WPI) (Provon 190 from Glanbia PLC) and with Bovine Serum Albumin for comparison purposes. These are described as Test+0.2% or Test+0.4% WPI or BSA.

Raji B lymphocytes were grown as described in the Methods and viability after a 60 minute exposure to the various test solutions was assessed using an Invitrogen Countess Cell Viability meter as described in the Methods. The results are presented in Table 23 below.

TABLE 23

Reduction in cell viability at 60 minute exposure to test items
Raji B Lymphocytes

| | control | Buffer blank | Test | Test + 0.2% DLL | Test + 0.4% DLL | Test + 0.2% WPI | Test + 0.4% WPI | Test + 0.2% BSA | Test + 0.4% BSA |
|---|---|---|---|---|---|---|---|---|---|
| % Viable T zero | 78 | 72 | 75 | 77 | 73 | 76 | 79 | 75 | 71 |
| % Viable T 60 min | 72 | 69 | 12 | 59 | 68 | 48 | 53 | 19 | 21 |
| % cell survival | 92 | 96 | 16 | 77 | 93 | 63 | 67 | 25 | 30 |

The % cell survival in the test item is just 16% after 60 minutes. By comparison, the control consisting of Raji B cells in cell culture media lost just 8% viability and the buffer blank being 100 mM sodium citrate at pH 4.5 was even less at 4% reduction. With the addition of 0.2% and 0.4% free membrane lipid (de-lipidised lecithin) % cell survival in the test was increased from 16% to 77% and 93%, and although not quite as effective, the addition of free WPI increased cell survival from 16% to 63% and 67%. Bovine serum albumin was considerably less effective in protecting against cell damage.

The inclusion of free membrane lipid in an aqueous dispersion of membrane lipid emulsion has no significant effect on the microbicidal properties of the membrane lipid emulsion. A late log phase culture of the yeast *Candida albicans* grown as described in the Methods contained $1.33 \times 10^7$ viable cells per ml. This was used to inoculate aliquots of each test item from above at a dilution of 1:10 such that each ml of test item contained in excess of 6 logs of yeast cells. Samples were withdrawn over time periods of up to 10 minutes and assessed for residual viability using the procedures described in the Methods. As illustrated in Table 24 below, detectable viability was eradicated in less than 5 minutes by all test items.

*Helicobacter pylori* was grown on Columbia Blood Agar supplemented with 5% de-fibrinated sheep blood in an anaerobic jar using Anaerogen low oxygen gas packs from Oxoid UK. *Salmonella typhimurium* and *E. coli* K12 were grown on Brain Heart Infusion agar as described in the Methods.

The microbicidal efficacy of the re-constituted milk supplemented with the three individually emulsified free fatty acids was determined using the Minimum Inhibitory Concentration (MIC) method of agar dilution described in the methods. Dilutions of the re-constituted skim milk were prepared in sterile distilled water such that further dilutions of aliquots of these in cooled agar provided an agar with combined free fatty acid concentrations ranging from 1% to 0.1% in 0.1% increments and from 0.1% to 0.01% in increments of 0.01%. Cultures of the three test organisms were inoculated onto these plates and incubated according to culture requirements: *Helicobacter* under low oxygen tension, *Salmonella* and *E. coli* under aerobic conditions all at 37° C.

The minimum Inhibitory Concentration, being the lowest dilution where no growth was observed was greater than 0.5% for *Helicobacter* and greater than 0.1% for both *Salmonella* and *E. coli*.

TABLE 24

Microbicidal Effect of Free Membrane Lipid in Membrane Lipid Emulsions
Time to kill greater than 6 logs *Candida albicans*.

| | control | Buffer blank | Test | Test + 0.2% DLL | Test + 0.4% DLL | Test + 0.2% WPI | Test + 0.4% WPI | Test + 0.2% BSA | Test + 0.4% BSA |
|---|---|---|---|---|---|---|---|---|---|
| Time Mins | NA | NA | <5 | <5 | <5 | <5 | <5 | >5 | >5 |

Example 18

Use in a Medical Food

Separate emulsions of caprylic, capric and lauric acid were prepared as 5.0% W/V fatty acid emulsified in 4.0% de-lipidised lecithin as described in the Methods. The individual emulsions were mixed in a ratio of 1:1:1.

Marvel skim milk powder from Premier International Foods (UK) Ltd, Spalding, Lincolnshire, England was re-constituted using 90% of the water volume according to the manufacturer's instructions. Once fully hydrated 10% by volume of the combined mix of separately emulsified free fatty acids was added and mixed by stirring, bringing the total volume to 100%.

The invention claimed is:
1. A method of treating or preventing a microbial infection and regulating the rate of blood-clotting in a subject in need thereof, the method comprising administering to the subject an effective amount of an antimicrobial and blood-clotting regulatory composition for use in blood contact applications selected from the group consisting of surgical irrigation, wound care, catheter locking solutions, and the coating of catheters and other medical devices for insertion through the skin or into a bodily orifice or cavity, the composition comprising:
   (a) one or more free fatty acids selected from the group consisting of caproic, caprylic, capric, lauric, palmitic, stearic, oleic, linoleic and linolenic acids and mixtures thereof; and

(b) one or more membrane lipids as emulsifying agent for the free fatty acid(s), wherein the membrane lipid is delipidized lecithin, wherein the ratio of component (a) to component (b) is from about 0.25:1 to about 10:1.

2. The method of claim 1, wherein the free fatty acid is selected from one or more of caproic, caprylic, capric and lauric acids.

3. The method of claim 1, wherein the free fatty acid is caprylic acid.

4. The method of claim 1, wherein the ratio of component (a) to component (b) is; or from about 0.5:1 to about 10:1, or from about 0.5:1 to about 5.0:1, or from about 1.0:1 to about 2.5:1, or from about 1.25:1 to about 2.5:1, on a weight for weight basis.

5. The method of claim 1, wherein the composition further comprises one or more pharmaceutically acceptable organic acids or a pharmaceutically acceptable salt or ester thereof; and/or one or more pharmaceutically acceptable inorganic acid salts.

6. The method of claim 5, wherein the organic acid is selected from acetic, pyruvic, propionic, glycolic, oxalic, lactic, glyceric, tartronic, malic, maleic, ascorbic, fumaric, tartaric, malonic, glutaric, propenoic, cis or trans butenoic and citric acids and mixtures thereof, and pharmaceutically acceptable salts and esters thereof.

7. The method of claim 5, wherein the organic acid is citric or lactic acid or the sodium or potassium salt thereof; or wherein the organic acid salt is sodium citrate.

8. The method of claim 1, wherein the composition is administered in a catheter locking solution.

9. The method of claim 8, wherein the catheter locking solution further comprises dextran.

10. The method of claim 1, wherein the composition is administered in a coating on the surface of a catheter or other medical device for insertion through the skin or into a bodily orifice or cavity.

11. The method of claim 1 for treating a wound, the method comprising irrigating the wound with a surgical irrigation fluid comprising the composition as defined in claim 1.

12. The method of claim 1, wherein the microbial infection is treated or prevented by disrupting microbial biofilm or inhibiting its formation, respectively.

* * * * *